United States Patent

Yan et al.

(10) Patent No.: US 9,108,954 B2
(45) Date of Patent: Aug. 18, 2015

(54) SYNTHESIS PROCESS OF DASATINIB AND INTERMEDIATE THEREOF

(75) Inventors: Rong Yan, Nanjing (CN); Hao Yang, Nanjing (CN); Wen Hou, Nanjing (CN); Yongxiang Xu, Nanjing (CN)

(73) Assignees: Nan Jing Cavendish Bio-Engineering Technology Co., Ltd., Jiangsu (CN); Rong Yan, Jiangsu (CN)

( * ) Notice: Subject to any disclaimer, the term of this patent is extended or adjusted under 35 U.S.C. 154(b) by 261 days.

(21) Appl. No.: 13/576,637

(22) PCT Filed: Jan. 30, 2011

(86) PCT No.: PCT/CN2011/070828
§ 371 (c)(1),
(2), (4) Date: Aug. 20, 2012

(87) PCT Pub. No.: WO2011/095126
PCT Pub. Date: Aug. 11, 2011

(65) Prior Publication Data
US 2013/0030177 A1    Jan. 31, 2013

(30) Foreign Application Priority Data

Feb. 2, 2010  (CN) .......................... 2010 1 0104295
Apr. 26, 2010  (CN) .......................... 2010 1 0169637

(51) Int. Cl.
*C07D 417/12*    (2006.01)
*C07D 417/14*    (2006.01)

(52) U.S. Cl.
CPC ................................... *C07D 417/12* (2013.01)

(58) Field of Classification Search
CPC ........................... C07D 417/12; C07D 417/14
USPC .................................................. 544/295, 328
See application file for complete search history.

(56) References Cited

U.S. PATENT DOCUMENTS

2009/0118297 A1    5/2009  Simo et al.

FOREIGN PATENT DOCUMENTS

| CN | 1348370 A | 5/2002 |
| CN | 1980909 A | 6/2007 |
| CN | 101597284 A | 12/2009 |
| CN | 101812060 A | 8/2010 |
| CN | 101845045 A | 9/2010 |
| WO | 2007106879 A2 | 9/2007 |

OTHER PUBLICATIONS

Wang, Wei, et al. Study of synthetic process of dasatinib, Chinese Journal of Medicinal Chemistry, Feb. 2009, vol. 19, No. 1, pp. 36-38.
International Search Report dated May 5, 2011 from International Patent Application No. PCT/CN2011/070828 filed Jan. 30, 2012 (10 pages).
Das, et al. '2-Aminothiazole as a Novel Kinase Inhibitor Temple. Structure-Activity Relationship Studies toward the Discovery of N-(2-chloro-6-methylphenyl)-2-[[6-[4-(2-hydroxyethyl)-1-pyperizinyl)]-2-methyl-4-pyrimidinyl] amino)]-1,3-thiazole-5-carboxamide', Journal of Medicinal Chemistry, 2006, vol. 49, pp. 6819-6832.

*Primary Examiner* — James O Wilson
*Assistant Examiner* — Ebenezer O Sackey
(74) *Attorney, Agent, or Firm* — Sunstone IP

(57) ABSTRACT

Synthesis process of dasatinib is disclosed, which includes the step of reacting the compound of formula I with that of formula II to obtain the compound of formula III. Also disclosed is the compound of formula III which is used as an intermediate for synthesizing dasatinib. The substituents of $R_1$, $R_2$, $R_3$ or $R_4$ in formulae I, II or III are defined as in the description.

8 Claims, 1 Drawing Sheet

US 9,108,954 B2

SYNTHESIS PROCESS OF DASATINIB AND INTERMEDIATE THEREOF

TECHNICAL FIELD

The present invention is in the field of pharmaceutical chemistry, and more specifically it relates to a novel method for synthesizing high-purity Dasatinib simply and intermediates thereof.

BACKGROUND ART

Dasatinib, with the trade name SPRYCEL™, is a oral tyrosine kinase to inhibitor and developed by BMS Company. It is used to cure adult chronic myelogenous leukemia (CML), and acute lymphatic leukemia (ALL) with positive Philadelphia chromosome, etc. Its chemical name is N-(2-chloro-6-methylphenyl)-2-[[6-[4-(2-hydroxyethyl)-1-piperazinyl]-2-methyl-4-pyrimidyl]amino]-5-thiazolformamide and its chemical structure is as following:

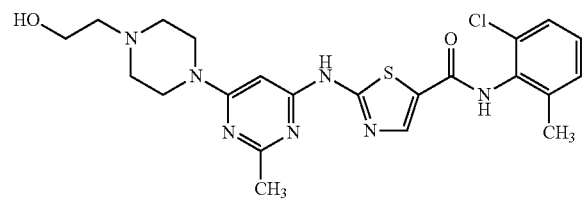 [SMILES: Cc1nc(Nc2ncc(C(=O)Nc3c(C)cccc3Cl)s2)cc(N2CCN(CCO)CC2)n1]

A method for synthesizing Dasatinib was disclosed by J•Das in the China patent application, which was published on 8 May 2002 with the public number CN 1348370A. According to this method, ethyl 2-[(tert-butoxycarbonyl)amino]thiazole-5-carboxylate was original raw material, and Dasatinib was synthesized through the following route:

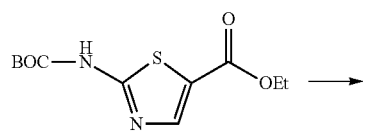

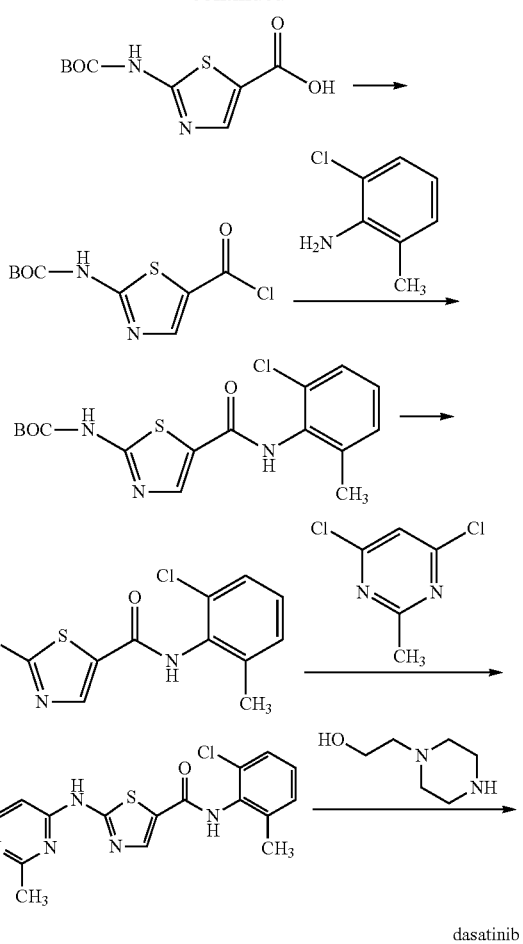

In addition, another method for synthesizing Dasatinib was disclosed by Chen Bangchi in the China patent application, which was published on 13 Jun. 2007 with the public number CN 1980909A. According this method isocyanate or thiourea was used to form thiazole ring to synthesize Dasatinib.

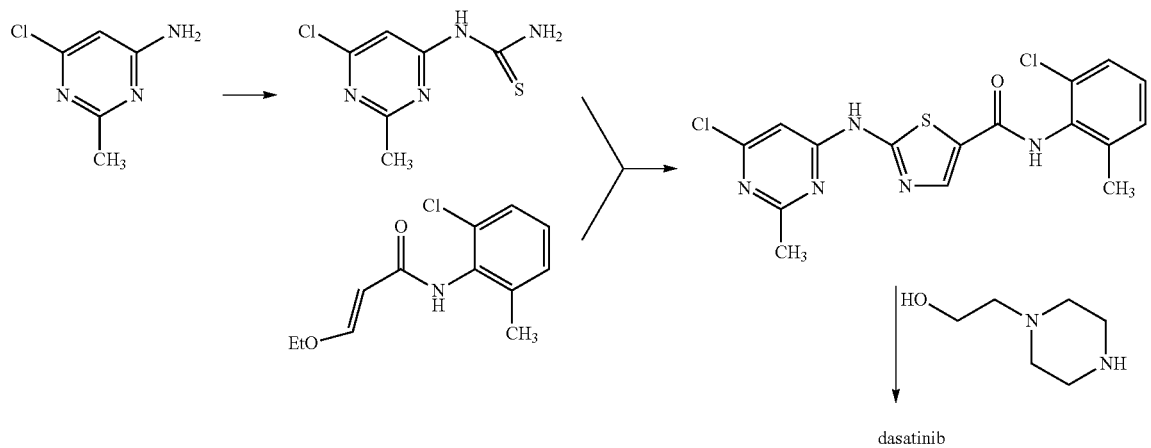

Alternatively

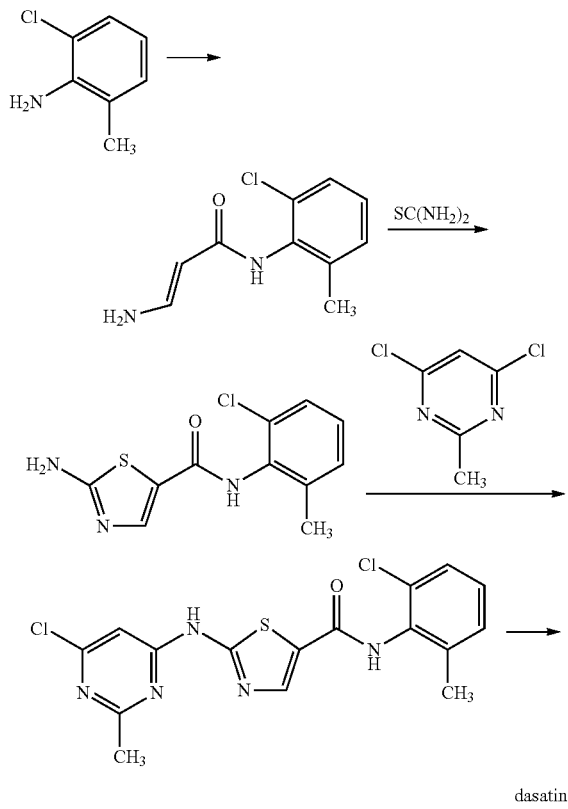

dasatinib

Another method for synthesizing Dasatinib was described by Li et al. in the International patent application, which was published on 20 Sep. 2007 (publication number WO 2007/106879 A2). According this method another thiourea derivatives was used to form thiazole ring, in which amino groups were protected by triphenylmethyl, and then deprotection, and reaction with 2-methyl-4,6-dichloropyrimidine and 1-(2-hydroxyethyl)-piperazine to to synthesize Dasatinib.

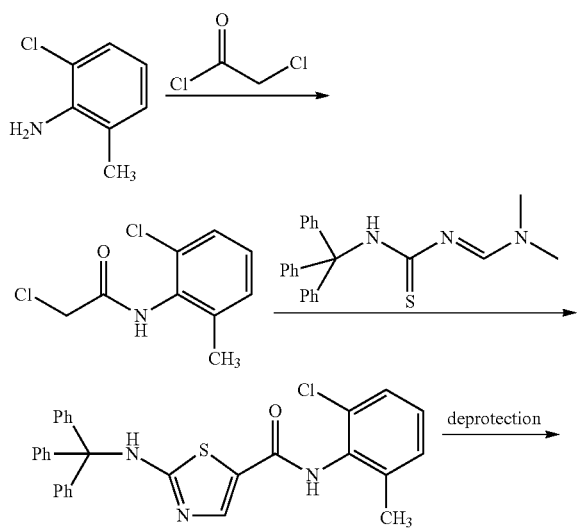

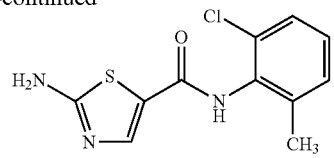

Another method for synthesizing Dasatinib was disclosed by Das et al. in the document: '2-Aminothiazole as a Novel Kinase Inhibitor Temple. Structure-Activity Relationship Studies toward the Discovery of N-(2-chloro-6-methylphenyl)-2-[[6-[4-(2-hydroxyethyl)-1-pyperizinyl]-2-methyl-4-pyrimidinyl]amino]-1,3-thiazole-5-carboxamide', *J. Med. Chem.* 2006, 49: 6819-6832. By this method 2-chlorothiazole was the original raw material and 4-methoxyphenmethyl was adopted to protect amino group to synthesize Dasatinib:

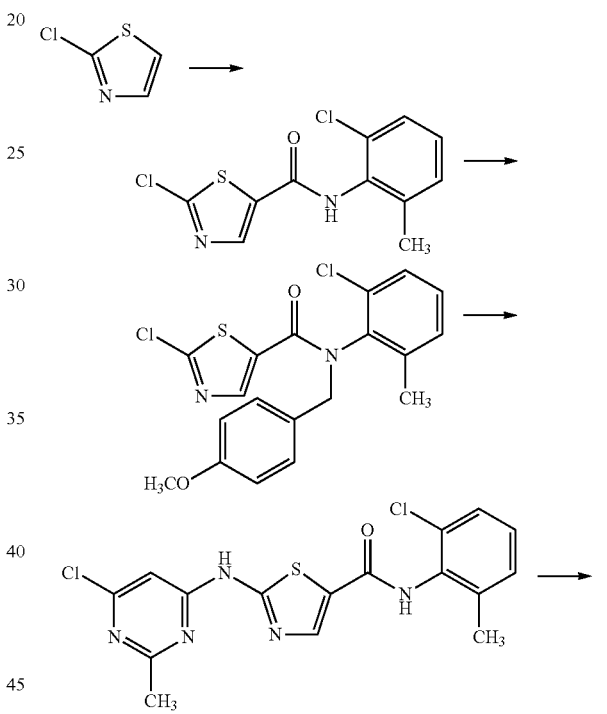

dasatinib

However, desires still exist in this field: a new method suitable for industrial production and by the method easily available raw material is adopted to synthesize Dasatinib of high purity simply.

SUMMARY OF INVENTION

After a large amount of researches, the inventor successfully developed a simple method suitable for industrial production and by the method easily available raw material is adopted as original substances to synthesize Dasatinib, which overcame the disadvantages described above in prior art.

One objective of the present invention is to provide a method for synthesizing Dasatinib.

Another objective of the present invention is to provide the intermediates used to synthesize Dasatinib.

A third objective of the present invention is to provide the preparation method to yield Dasatinib of high purity.

DETAILED DESCRIPTION OF INVENTION

A method for synthesizing Dasatinib is provided in this invention, including the following steps: the compound of Formula I reacts with the compound of Formula II to yield the compound of Formula III.

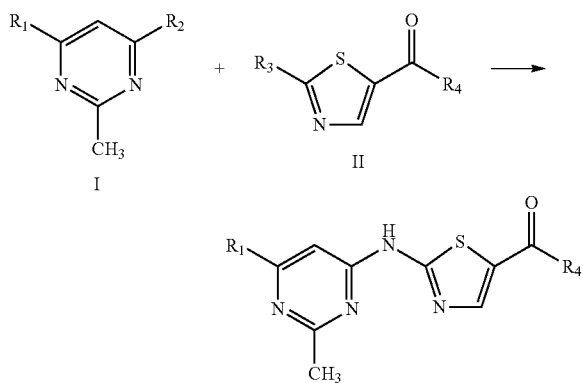

Wherein, in Formula I and III, $R_1$ and $R_2$ are each independently selected from halogen (i.e. fluorine, chlorine, bromine or iodine), 4-(2-hydroxyethyl)piperazine-1-yl or hydroxyl-protected 4-(2-hydroxyethyl)piperazine-1-yl; $R_1$ and $R_2$ can be identical or different, with the proviso that they can not simultaneously be 4-(2-hydroxyethyl)piperazine-1-yl or hydroxyl-protected 4-(2-hydroxyethyl)piperazine-1-yl; preferably, $R_1$ is selected from halogen (i.e. fluorine, chlorine, bromine or iodine), 4-(2-hydroxyethyl)piperazine-1-yl or hydroxyl-protected 4-(2-hydroxyethyl)piperazine-1-yl, and $R_2$ is selected from halogen (i.e. fluorine, chlorine, bromine or iodine) or amino; herein, the described hydroxyl-protecting group, which is well known by person skilled in this field, can be selected from ether, C1-C4 alkyl acid esters or substituted C1-C4 alkyl acid esters, or carbonates protecting groups; the described ether is selected from substituted or unsubstituted C1-C4 alkyl ether, substituted or unsubstituted benzyl ether and silyl ether; the described substituted C1-C4 alkyl ether is selected from substituted methyl ether or ethyl ether, more preferably, selected from methoxymethyl ether, t-butoxymethyl ether, 2-methoxyethoxymethyl ether, methylthiomethyl ether, (phenyldimethylsilyl)methoxymethyl ether, benzyloxymethyl ether, (4-methoxylphenoxy)methyl ether, menthoxymethyl ether, tetrahydropyranyl ether, tetrahydrofuranyl ether, 1-ethoxyethyl ether, and ally ether; the described substituted benzyl ether is selected from 4-methoxybenzyl ether, 3,4-dimethoxybenzyl ether, and p-nitrobenzyl ether; the described silyl ether is selected from diisopropylsilyl ether, t-butyldimethylsilyl ether, and t-butyldiphenylsilyl ether; the described alkyl acid esters are selected from formacyl, acetyl, propionyl, butyryl, benzoyl, and p-phenylbenzoyl; the described carbonates are selected from methoxymethyl ester, 9-fluorenylmethyl ester, 2-(trimethylsilyl)ethyl ester, isobutyl ester, vinyl ester, allyl ester, p-nitrophenyl ester and benzyl ester, which are detailed on Page 16-366 of 'GREENE'S PROTECTIVE GROUP IN ORGANIC SYNTHESIS' fourth edition written by PETER G. M. WUT et al., 2007, A John Wiley & Sons, Inc., Publication;

in Formula II and III, $R_3$ is selected from halogen (i.e. fluorine, chlorine, bromine or iodine) or amino; with the proviso that when $R_2$ is selected from halogen (i.e. fluorine, chlorine, bromine or iodine), $R_3$ is amino, and when $R_2$ is amino, $R_3$ is selected from halogen (i.e. fluorine, chlorine, bromine or iodine);

in Formula II and Formula III, $R_4$ is C1-C6 alkoxy or substituted C1-C6 alkoxy, wherein, the described substituted groups are selected from the group consisting of C1-C6 alkyl, aryl or substituted aryl; the described aryl groups are selected from phenyl; the described substituted aryl groups are phenyl substituted by one or more of groups which are selected from C1-C4 alkyl or alkoxy, and halogen or nitro, preferably, $R_4$ is methoxy, benzyloxy, ethoxyl, propoxy, isopropoxy, butoxy, t-butoxy, sec-butoxy, isobutoxy, pentyloxy or hexyloxy;

with the proviso that the described synthetic method does not include that when $R_1$ and $R_2$ are both chloride and $R_3$ is amino, the compound of Formula I reacts with the compound of Formula II to yield the compound of Formula III.

In one embodiment of this invention, when $R_1$ in Formula I and III is halogen (i.e. fluorine, chlorine, bromine or iodine), the above-described synthetic method provided in the present invention further includes that the compound of Formula III is hydrolyzed to yield the compound of Formula IV:

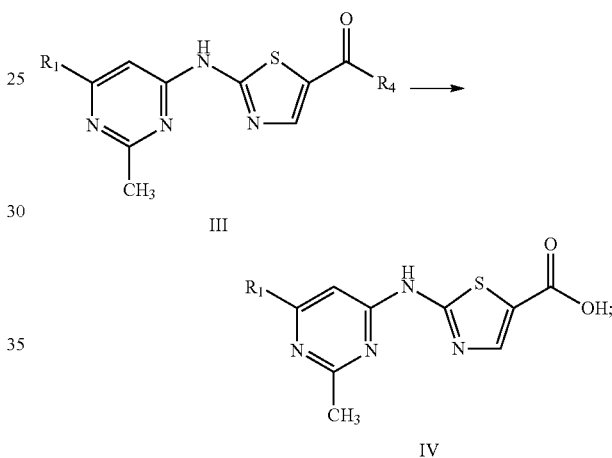

wherein, the definition of $R_4$ in Formula III is as above;

subsequently, by the action of chlorination agents the compound of Formula IV is converted to yield the compound of Formula V;

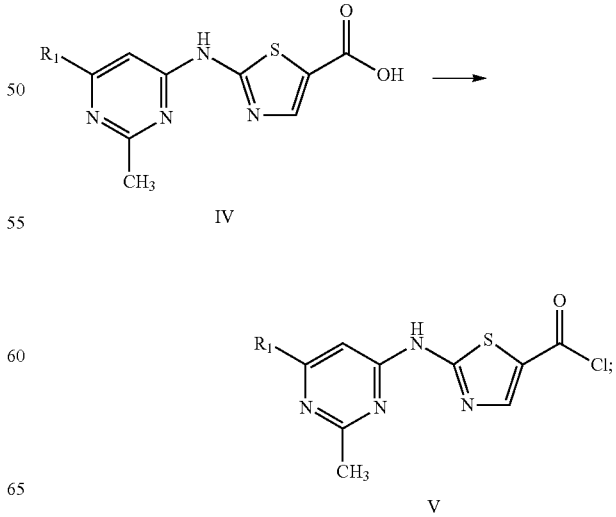

then, the compound of Formula V reacts with 2-chloro-6-methylaniline to yield the compound of Formula VI;

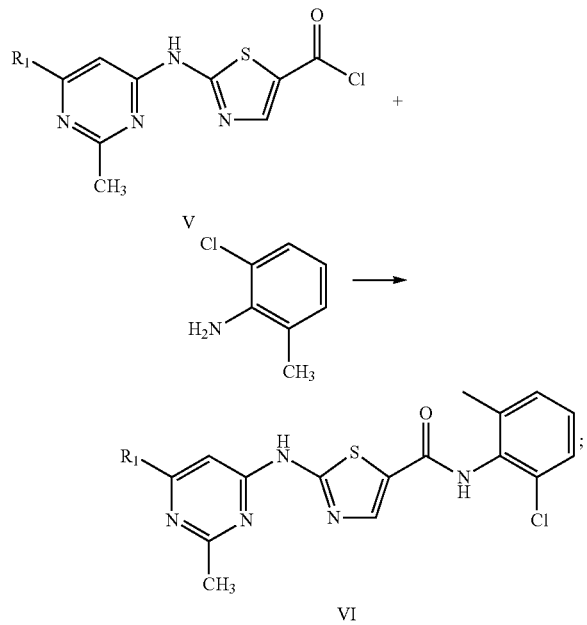

alternatively, the compound of Formula IV reacts with 2-chloro-6-methylaniline in the presence of an amidation condensing agent to yield the compound of Formula VI; wherein R1 in Formula IV, Formula V and Formula VI is halogen;

then the compound of Formula VI reacts with 1-(2-hydroxyethyl)piperazine to yield Dasatinib;

preferably, in the described synthetic method, the described chlorination agents are selected from phosphorus trichloride, phosphorus pentachloride, thionyl chloride and oxalyl chloride, preferably oxalyl chloride;

preferably, in the described synthetic method, the described amidation condensing agent is selected from phosphorodichloridic acid phenyl ester (PDCP), dicyclohexylcarbodiimide (DCC), diisopropylcarbodiimide (DIC), 2-(7-aza-1H-benzotriazole-1-yl)-N,N,N',N'-tetramethyluronium hexafluorophosphate (HATU), and 1-(3-dimethylaminopropyl)-3-ethylcarbodiimide (EDCI).

In another embodiment of this invention, when $R_1$ in Formula I and III is halogen (i.e. Fluorine, chlorine, bromine or iodine), the above-described synthetic method provided in the present invention further includes that the compound of Formula III reacts with 1-(2-hydroxyethyl)piperazine to yield compound of Formula VII:

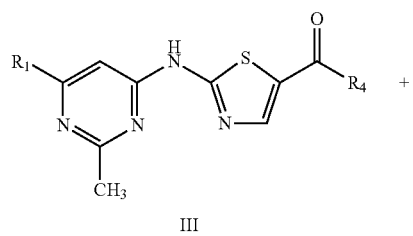

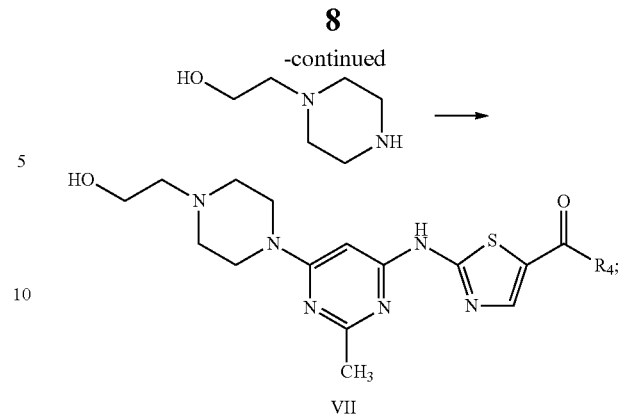

wherein, the definition of $R_4$ in Formula III and Formula VII is as above;

then the compound of Formula VII is hydrolyzed to yield the compound of Formula VIII:

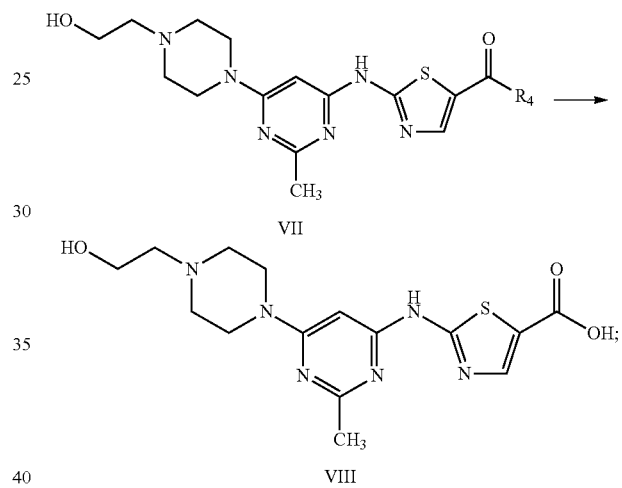

the compound of Formula VIII reacts with a hydroxyl protection agent to yield the compound of Formula IX:

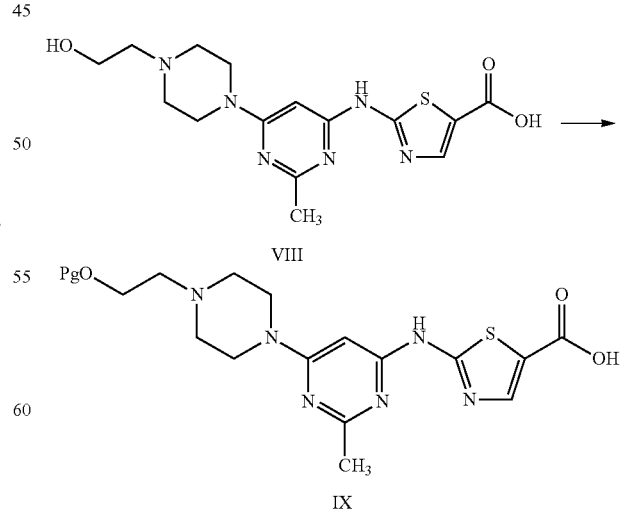

the compound of Formula IX is converted to be the compound of Formula X by the action of chlorination agents:

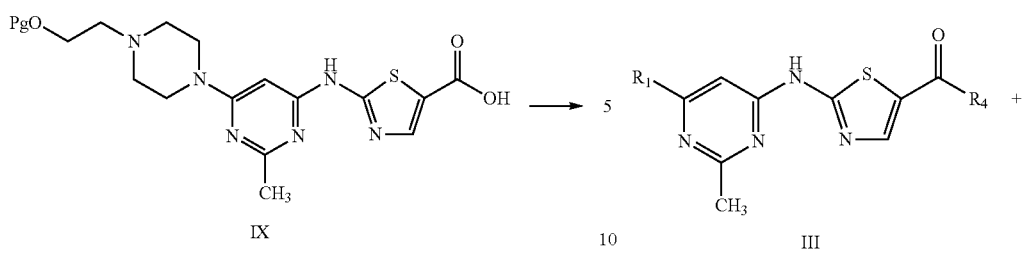

IX

X

III

XI

Pg in Formula IX and Formula X is a hydroxyl protection group, and the compound of Formula X reacts with 2-chloro-6-methylaniline and then the protecting group Pg boned to hydroxyl group is removed to yield Dasatinib;

alternatively, the compound of Formula IX reacts with 2-chloro-6-methylaniline in the presence of an amidation condensing agent, and then the protecting group Pg boned to hydroxyl group is removed to yield Dasatinib;

preferably, in the described synthetic method of Dasatinib, the described hydroxyl protection agents are as the following: C1-C4 alkyl acid esters or substituted C1-C4 alkyl acid esters, or carbonates protecting groups; the described alkyl acid esters are selected from formacyl, acetyl, propionyl, butyryl, benzoyl, and p-phenylbenzoyl; the described carbonates are selected from methoxymethyl ester, 9-fluorenylmethyl ester, 2-(trimethylsilyl)ethyl ester, isobutyl ester, vinyl ester, allyl ester, n-nitrophenyl ester and benzyl ester, which are detailed on Page 16-366 of 'GREENE'S PROTECTIVE GROUP IN ORGANIC SYNTHESIS' Fourth edition written by PETER G. M. WUT et al., 2007, A John Wiley & Sons, Inc., Publication;

preferably, in the described synthetic method of Dasatinib, the described chlorination agent is selected from phosphorus trichloride, phosphorus pentachloride, thionyl chloride or oxalyl chloride, preferably oxalyl chloride;

preferably, in the described synthetic method of Dasatinib, the described amidation condensing agent is selected from phosphorodichloridic acid phenyl ester (PDCP), dicyclohexylcarbodiimide (DCC), diisopropylcarbodiimide (DIC), 2-(7-aza-1H-benzotriazole-1-yl)-N,N,N',N'-tetramethyluronium hexafluorophosphate (HATU), and 1-(3-dimethylaminopropyl)-3-ethylcarbodiimide (EDCI).

In the embodiments of this invention, when $R_1$ in Formula I and III is halogen (i.e. fluorine, chlorine, bromine or iodine), the above-described synthetic method provided in the present invention further includes that the compound of Formula III reacts with hydroxyl-protected 1-(2-hydroxyethyl)piperazine to yield compound of Formula XI:

wherein, the definition of $R_4$ in Formula III and Formula XI is as above; Pg is a hydroxyl protecting group rather than hydrogen;

then the compound of Formula XI is hydrolyzed to yield the compound of Formula IX.

XI

IX the compound of Formula IX is converted to be the compound of formula X by the action of chlorination agents:

IX

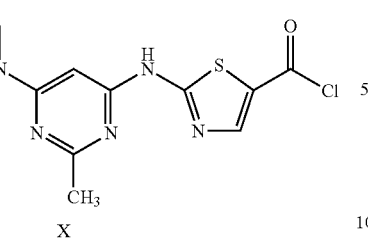

X the compound of Formula X reacts with 2-chloro-6-methylaniline and then the protecting group of Pg is removed to yield Dasatinib;

alternatively, the compound of Formula IX reacts with 2-chloro-6-methylaniline in the presence of an amidation condensing agent, and then the protecting group Pg boned to hydroxyl group is removed to yield Dasatinib, wherein Pg in Formula IX and Formula X is a hydroxyl protecting group rather than hydrogen;

preferably, in the described synthetic method of Dasatinib, the described hydroxyl-protecting group is an ether protection group, which is selected from substituted or unsubstituted C1-C4 alkyl ether, substituted or unsubstituted benzyl ether and silyl ether; the described substituted C1-C4 alkyl ether is preferably selected from substituted methyl ether and ethyl ether, more preferably, selected from methoxymethyl ether, t-butoxymethyl ether, 2-methoxyethoxymethyl ether, methylthiomethyl ether, (phenyldimethylsilyl)methoxymethyl ether, benzyloxymethyl ether, (4-methoxylphenoxy) methyl ether, menthoxymethyl ether, tetrahydropyranyl ether, tetrahydrofuranyl ether, 1-ethoxyethyl ether, and ally ether; the described substituted benzyl ether is preferably selected from methoxybenzyl ether, 3,4-dimethoxybenzyl ether, and p-nitrobenzyl ether; the described silyl ether is preferably selected from diisopropylsilyl ether, t-butyldimethyl silyl ether, and t-butyldiphenyl silyl ether, which is detailed in Page 16-366 of 'GREENE'S PROTECTIVE GROUP IN ORGANIC SYNTHESIS', Fourth edition, written by PETER G. M. WUT et al., 2007, A John Wiley & Sons, Inc., Publication;

preferably, in the described synthetic method of Dasatinib, the described chlorination agent is selected from phosphorus trichloride, phosphorus pentachloride, thionyl chloride and oxalyl chloride, preferably oxalyl chloride;

preferably, in the described synthetic method of Dasatinib, the described amidation condensing agent is selected from phosphorodichloridic acid phenyl ester (PDCP), dicyclohexylcarbodiimide (DCC), diisopropylcarbodiimide (DIC), 2-(7-aza-1H-benzotriazole-1-yl)-N,N,N',N'-tetramethyluronium hexafluorophosphate (HATU), and 1-(3-dimethylaminopropyl)-3-ethylcarbodiimide (EDCI).

In the embodiments of this invention, when $R_1$ in Formula III is 4-(2-hydroxyethyl)piperazin-1-yl or hydroxyl-protected 4-(2-hydroxyethyl)piperazin-1-yl, the above-described synthetic method provided in the present invention further includes that the compound of Formula III (i.e. the compound of Formula XI) is hydrolyzed to yield the compound of Formula IX

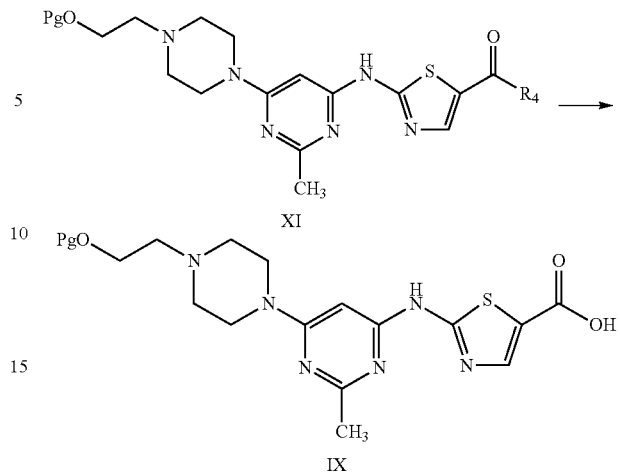

wherein, Pg in Formula IX or XI is hydroxyl protecting group or hydrogen, the definition of $R_4$ in Formula XI is as above; the compound of Formula IX is converted to be the compound of formula X by the action of chlorination agents:

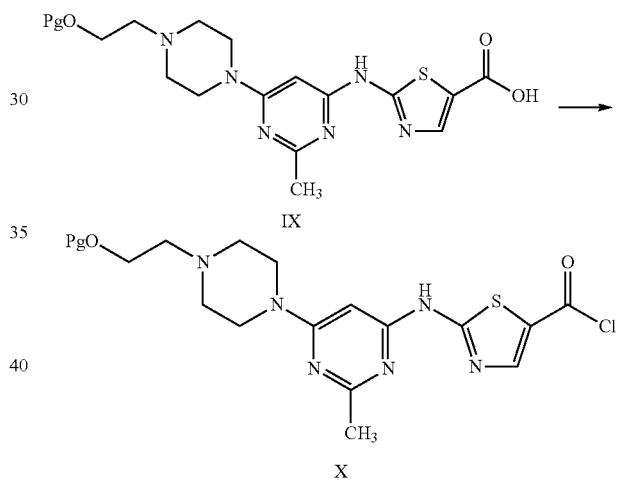

the compound of Formula X reacts with 2-chloro-6-methylaniline and then the protecting group Pg boned to hydroxyl group is removed to yield Dasatinib;

alternatively, the compound of Formula IX reacts with 2-chloro-6-methylaniline in the presence of an amidation condensing agent, and then the protecting group Pg boned to hydroxyl group is removed to yield Dasatinib;

preferably, in the described synthetic method of Dasatinib, the described hydroxyl-protecting group is an ether protection group, which is selected from substituted or unsubstituted C1-C4 alkyl ether, substituted or unsubstituted benzyl ether and silyl ether; the described substituted C1-C4 alkyl ether is preferably selected from substituted methyl ether and ethyl ether, more preferably, selected from methoxymethyl ether, t-butoxymethyl ether, 2-methoxyethoxymethyl ether, methylthiomethyl ether, (phenyldimethylsilyl)methoxymethyl ether, benzyloxymethyl ether, (4-methoxylphenoxy) methyl ether, menthoxymethyl ether, tetrahydropyranyl ether, tetrahydrofuranyl ether, 1-ethoxyethyl ether, and ally ether; the described substituted benzyl ether is preferably selected from methoxybenzyl ether, 3,4-dimethoxybenzyl ether, and p-nitrobenzyl ether; the described silyl ether is preferably selected from diisopropylsilyl ether, t-butyldimethyl silyl ether, and t-butyldiphenyl silyl ether, which is detailed in Page 16-366 of 'GREENE'S PROTECTIVE GROUP IN ORGANIC SYNTHESIS', Fourth edition, written by PETER G. M. WUT et al., 2007, A John Wiley & Sons, Inc., Publication;

preferably, in the described synthetic method of Dasatinib, the described chlorination agent is selected from phosphorus trichloride, phosphorus pentachloride, thionyl chloride and oxalyl chloride, preferably oxalyl chloride.

In the embodiments of this invention, the above-described synthetic method provided in the present invention further includes that the compound of Formula III reacts with 2-chloro-6-methylaniline to yield compound of Formula XII:

[Structure III]

[Structure of 2-chloro-6-methylaniline]

[Structure XII]

wherein, $R_1$ in Formula III and XII is selected from halogen (i.e. fluorine, chlorine, bromine or iodine), 4-(2-hydroxyethyl)piperazine-1-yl or hydroxyl-protected 4-(2-hydroxyethyl)piperazine-1-yl; $R_4$ in Formula III is defined as above;

when $R_1$ is halogen, the compound of Formula XII is exactly the compound of Formula VI, and then the above-described method can be adopted to synthesize Dasatinib;

when $R_1$ is 4-(2-hydroxyethyl)piperazine-1-yl, the compound of Formula XII is exactly Dasatinib;

when $R_1$ is hydroxyl-protected 4-(2-hydroxyethyl)piperazine-1-yl, hydroxyl protection group is removed to yield Dasatinib.

In the described-above embodiments provided by this invention, deprotection of the described hydroxyl protecting group, likewise, can refer to Page 16-366 of 'GREENE'S PROTECTIVE GROUP IN ORGANIC SYNTHESIS', Fourth edition, written by PETER G. M. WUT et al., 2007, A John Wiley & Sons, Inc., Publication; the technicians of this field can hereby choose proper deprotection conditions.

In addition, the present invention provides the intermediate compound, i.e. the compound of Formula XIII, which is used to synthesize Dasatinib:

[Structure XIII]

wherein, $R_1$ is selected from halogen, 4-(2-hydroxyethyl)piperazine-1-yl and hydroxyl-protected 4-(2-hydroxyethyl)piperazine-1-yl, and with the proviso that $R_1$ is not chlorine;

$R_4$ is hydroxyl, C1-C6 alkoxy or substituted C1-C6 alkoxy, or halogen, wherein the described substituted groups are selected from the group consisting of C1-C6 alkyl, aryl or substituted aryl; the described aryl groups are selected from phenyl; the described substituted aryl groups are substituted phenyls substituted by one or more groups which are selected from C1-C4 alkyl or alkoxy, and halogen and nitro, preferably, $R_4$ is hydroxyl, methoxy, benzyloxy, ethoxyl, propoxy, isopropoxy, butoxy, t-butoxy, sec-butoxy, isobutoxy, pentyloxy, hexyloxy chlorine or bromine;

preferably, the compound of Formula XIII described in the present invention, in which:

$R_1$ is selected from fluorine, bromine, iodine, 4-(2-hydroxyethyl)piperazine-1-yl and hydroxyl-protected 4-(2-hydroxyethyl)piperazine-1-yl, and with the proviso that $R_1$ is not chlorine; $R_4$ is hydroxyl, methoxy, benzyloxy, ethoxyl, propoxy, isopropoxy, butoxy, t-butoxy, sec-butoxy, isobutoxy, pentyloxy, hexyloxy chlorine or bromine.

more preferably, the compound of Formula XIII described in the present invention, in which:

$R_1$ is selected from 4-(2-hydroxyethyl)piperazine-1-yl and hydroxyl-protected 4-(2-hydroxyethyl)piperazine-1-yl; $R_4$ is hydroxyl, methoxy, benzyloxy, ethoxyl, propoxy, isopropoxy, butoxy, t-butoxy, sec-butoxy, isobutoxy, pentyloxy, hexyloxy chlorine or bromine.

The present invention provides the intermediate compound used to synthesize Dasatinib, which is selected from anyone of the following compounds:

methyl 2-(6-bromo-2-methylpyrimidin-4-ylamino)thiazole-5-formate;

ethyl 2-(6-bromo-2-methpyrimidin-4-ylamino)thiazole-5-formate;

isopropyl 2-(6-bromo-2-methylpyrimidin-4-ylamino)thiazole-5-formate;

methyl 2-(6-iodo-2-methylpyrimidin-4-ylamino)thiazole-5-formate;

ethyl 2-(6-iodo-2-methylpyrimidin-4-ylamino)thiazole-5-formate;

isopropyl 2-(6-iodo-2-methylpyrimidin-4-ylamino)thiazole-5-formate;

2-(6-bromo-2-methylpyrimidin-4-ylamino)thiazole-5-formic acid;

2-(6-iodo-2-methylpyrimidin-4-ylamino)thiazole-5-formic acid;

2-(6-bromo-2-methylpyrimidin-4-ylamino)thiazole-5-formyl chloride;

2-(6-iodo-2-methylpyrimidin-4-ylamino)thiazole-5-formyl chloride;

methyl 2-(6-(4-(2-hydroxyethyl)piperazin-1-yl)-2-methylpyrimidin-4-ylamino)thiazole-5-formate;

methyl 2-(6-(4-(2-acetoxyethyl)piperazin-1-yl)-2-methylpyrimidin-4-ylamino)thiazole-5-formate;

methyl 2-(6-(4-(2-bezoyloxyethyl)piperazin-1-yl)-2-methylpyrimidin-4-ylamino)thiazole-5-formate;
methyl 2-(6-(4-(2-benzoxyethyl)piperazin-1-yl)-2-methylpyrimidin-4-ylamino)thiazole-5-formate;
methyl 2-(6-(4-(2-para-methoxybenzoxyethyl)piperazin-1-yl)-2-methylpyrimidin-4-ylamino)thiazole-5-formate;
methyl 2-(6-(4-(2-(methoxymethoxy)ethyl)piperazin-1-yl)-2-methylpyrimidin-4-ylamino)thiazole-5-formate;
methyl 2-(6-(4-(2-(methylthiomethoxy)ethyl)piperazin-1-yl)-2-methylpyrimidin-4-ylamino)thiazole-5-formate;
methyl 2-(6-(4-(2-(ethoxyethoxy)ethyl)piperazin-1-yl)-2-methylpyrimidin-4-ylamino)thiazole-5-formate;
ethyl 2-(6-(4-(2-hydroxyethyl)piperazin-1-yl)-2-methylpyrimidin-4-ylamino)thiazole-5-formate;
ethyl 2-(6-(4-(2-acetoxyethyl)piperazin-1-yl)-2-methylpyrimidin-4-ylamino)thiazole-5-formate;
ethyl 2-(6-(4-(2-bezoyloxyethyl)piperazin-1-yl)-2-methylpyrimidin-4-ylamino)thiazole-5-formate;
ethyl 2-(6-(4-(2-benzoxyethyl)piperazin-1-yl)-2-methylpyrimidin-4-ylamino)thiazole-5-formate;
ethyl 2-(6-(4-(2-para-methoxybenzoxyethyl)piperazin-1-yl)-2-methylpyrimidin-4-ylamino)thiazole-5-formate;
ethyl 2-(6-(4-(2-(methoxymethoxy)ethyl)piperazin-1-yl)-2-methylpyrimidin-4-ylamino)thiazole-5-formate;
ethyl 2-(6-(4-(2-(methylthiomethoxy)ethyl)piperazin-1-yl)-2-methylpyrimidin-4-ylamino)thiazole-5-formate;
ethyl 2-(6-(4-(2-(ethoxyethoxy)ethyl)piperazin-1-yl)-2-methylpyrimidin-4-ylamino)thiazole-5-formate;
isopropyl 2-(6-(4-(2-hydroxyethyl)piperazin-1-yl)-2-methylpyrimidin-4-ylamino)thiazole-5-formate;
isopropyl 2-(6-(4-(2-acetoxyethyl)piperazin-1-yl)-2-methylpyrimidin-4-ylamino)thiazole-5-formate;
isopropyl 2-(6-(4-(2-bezoyloxyethyl)piperazin-1-yl)-2-methylpyrimidin-4-ylamino)thiazole-5-formate;
isopropyl 2-(6-(4-(2-benzoxyethyl)piperazin-1-yl)-2-methylpyrimidin-4-ylamino)thiazole-5-formate;
isopropyl 2-(6-(4-(2-para-methoxybenzoxyethyl)piperazin-1-yl)-2-methylpyrimidin-4-ylamino)thiazole-5-formate;
isopropyl 2-(6-(4-(2-(methoxymethoxy)ethyl)piperazin-1-yl)-2-methylpyrimidin-4-ylamino)thiazole-5-formate;
isopropyl 2-(6-(4-(2-(methylthiomethoxy)ethyl)piperazin-1-yl)-2-methylpyrimidin-4-ylamino)thiazole-5-formate;
isopropyl 2-(6-(4-(2-(ethoxyethoxy)ethyl)piperazin-1-yl)-2-methylpyrimidin-4-ylamino)thiazole-5-formate;
2-(6-(4-(2-hydroxyethyl)piperazin-1-yl)-2-methylpyrimidin-4-ylamino)thiazole-5-formic acid;
2-(6-(4-(2-acetoxyethyl)piperazin-1-yl)-2-methylpyrimidin-4-ylamino) thiazole-5-formic acid;
2-(6-(4-(2-bezoyloxyethyl)piperazin-1-yl)-2-methylpyrimidin-4-ylamino)thiazole-5-formic acid;
2-(6-(4-(2-benzoxyethyl)piperazin-1-yl)-2-methylpyrimidin-4-ylamino)thiazole-5-formic acid;
2-(6-(4-(2-para-methoxybenzoxyethyl)piperazin-1-yl)-2-methylpyrimidin-4-ylamino)thiazole-5-formic acid;
2-(6-(4-(2-(methoxymethoxy)ethyl)piperazin-1-yl)-2-methylpyrimidin-4-ylamino)thiazole-5-formic acid;
2-(6-(4-(2-(methylthiomethoxy)ethyl)piperazin-1-yl)-2-methylpyrimidin-4-ylamino)thiazole-5-formic acid;
2-(6-(4-(2-(ethoxyethoxy)ethyl)piperazin-1-yl)-2-methylpyrimidin-4-ylamino)thiazole-5-formic acid;
2-(6-(4-(2-hydroxyethyl)piperazin-1-yl)-2-methylpyrimidin-4-ylamino)thiazole-5-formyl chloride;
2-(6-(4-(2-acetoxyethyl)piperazin-1-yl)-2-methylpyrimidin-4-ylamino)thiazole-5-formyl chloride;
2-(6-(4-(2-bezoyloxyethyl)piperazin-1-yl)-2-methylpyrimidin-4-ylamino)thiazole-5-formyl chloride;
2-(6-(4-(2-benzoxyethyl)piperazin-1-yl)-2-methylpyrimidin-4-ylamino)thiazole-5-formyl chloride;
2-(6-(4-(2-para-methoxybenzoxyethyl)piperazin-1-yl)-2-methylpyrimidin-4-ylamino)thiazole-5-formyl chloride;
2-(6-(4-(2-(methoxymethoxy)ethyl)piperazin-1-yl)-2-methylpyrimidin-4-ylamino)thiazole-5-formyl chloride;
2-(6-(4-(2-(methylthiomethoxy)ethyl)piperazin-1-yl)-2-methylpyrimidin-4-ylamino)thiazole-5-formyl chloride;
or, 2-(6-(4-(2-(ethoxyethoxy)ethyl)piperazin-1-yl)-2-methylpyrimidin-4-ylamino)thiazole-5-formyl chloride.

This invention provides a method for purifying Dasatinib including:

after reaction, crude Dasatinib is yielded by condensation or suction filtration and added into an organic solvent;

it is dissolved by heating and stirring;

and a mixed solvent system of water and an organic medium is added dropwise;

the solid is precipitated completely when temperature reduces slowly to 0-10 by stirring and grow the grain; filtrate and collect the solid, and dry to give Dasatinib of high purity, which is greater than 99.50%.

In the above-described purifying method, the purity of the described crude Dasatinib is higher than 95%, preferably is higher than 97%.

In the above-described purifying method, the described organic solvent may be a non-protonic polar solvent, preferably is N,N-dimethylformamide, N,N-dimethylacetamide, dimethyl sulfoxide or the mixture of them.

In the above-described purifying method, the heating temperature in the described step of dissolving by heating and stirring is from room temperature to refluxing temperature, preferably 40-100.

In the above-described purifying method, the organic medium in the described step of adding mixed solvent system of water and an organic medium can be one kind of solvent or a mixed solvent of several kinds, to which Dasatinib is insoluble or slightly soluble.

In the purifying method of this invention, crude Dasatinib is dissolved in dimethylformamide or dimethylsulfoxide by heating, and when keeping certain temperature a certain amount of organic medium which Dasatinib is insoluble in or a mixture of that and water is added; after precipitation of Dasatinib by antisolvent crystallization, solid is obtained by filtration or centrifugation and high pure Dasatinib is got by dry.

In one embodiment of the purifying method of this invention, as crude Dasatinib, of which the impurity content is about 3%, is mixed with dimethylformamide or dimethylsulfoxide, the weight to volume ratio is generally 1:1~200 (g:ml), preferably 1:2~200, most preferably 1:3~200. Crude Dasatinibe is dissolved at the temperature from room temperature to heating, while the specific heating temperature can be lower than refluxing temperature, preferably lower than 120° C., most preferably lower than 100° C.; when keeping dissolving temperature, a certain amount of organic medium or a mixture of that and water, to which Dasatinib is insoluble, is added, and the volume ratio of the added organic medium or the mixture to dimethylformamide or dimethylsulfoxide is generally 1~200:1, preferably 2~200:1, most preferably 3~200:1, and the solid is precipitated by stirring and cool down to 0-10° C.; after heat preservation for 1-2 hours, filtrate and dry.

By Comparison with the Prior Art, the Advantage Technical Effects of this Invention Embody in:

1. Each synthetic route and method provided by this invention is simple, which is more benefit to industrial production.

In the synthetic route of this invention, source-widespread normal commercial materials can be adopted, for example, it is referred in route of this invention that normal commercial material 2-aminothiazole-5-formate is coupled with substituted halopiperazine, after that intermediate is hydrolyzed and then is coupled with 2-methyl-6-chloroaniline to give Dasatinib. What can be avoided is the complicated procedure in the prior art, by which the amino group of 2-aminothiazoleformate should be protected with Boc group before reaction. That the reaction steps are reduced from 6 to 4 not only reduces reaction steps and complicated synthetic processes, but also reduces output of the three wastes dramatically to be environment-friendly and low the cost evidently. Meanwhile the reaction conditions used in this invention are mild so to as to simplify workup and intermediates purification, which is more suitable to industrial manufacture.

2. By all of the existing synthetic methods for Dasatinib, 2-(6-chloro-2-methylpyrimidin-4-ylamino)-N-(2-chloro-6-methylphenyl)thiazole-5-formamide was first obtained using different synthetic routes or preparation ways and then condensed with 1-(2-hydroxyethyl)piperazine to get Dasatinib. While this invention provides a novel synthetic route, which can avoid to use 4-hydroxyethyl piperazine at the last step, so it's a simple route and method for synthesizing Dasatinib, which is more advantageous to control and increase product quality.

3. Yield of each step in the synthetic methods provided by this invention is high.

According to all of the existing methods recorded in the public data, yield is between 15% and 49%. When select the simplest synthetic path of this invention, for instance, select the route in this invention from Example 1 to Example 4: 2-methyl-4,6-dichloropyrimidine and 1-(2-hydroxyethyl)piperazine, which are raw materials and subjected four steps including condensation reaction and hydrolysis, are converted to Dasatinib, the total yield is higher than that of existing methods.

4. Because of the poor dissolvability of Dasatinib and the key intermediates thereof, it is difficult to prepare high-purity Dasatinib, which was hardly prepared by the existing synthetic routes. However, according to the process and purification methods provided by this invention Dasatinib of high purity, up to 99.9%, is yielded.

| Peak number | Retention time | Peak height | Peak area | Content |
|---|---|---|---|---|
| 1 | 5.873 | 97.721 | 1355.550 | 0.0032 |
| 2 | 8.582 | 1498534.125 | 41887600.00 | 99.9509 |
| 3 | 12.532 | 81.957 | 1653.400 | 0.0039 |
| 4 | 14.232 | 218.811 | 17573.600 | 0.0419 |
| Sum | | 1498932.615 | 41908182.550 | 100.000 |

Figure 2:
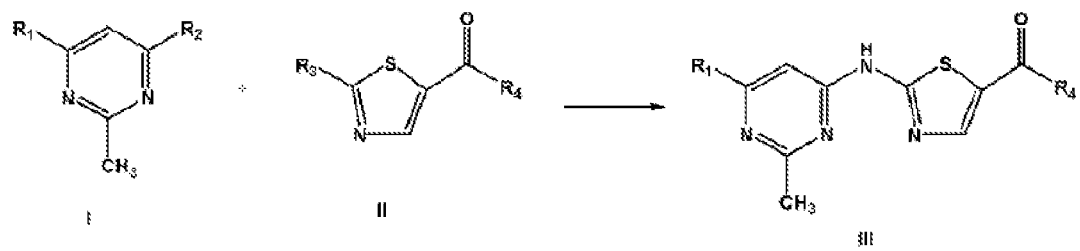

FIG. 2 represents the reaction between the compound of Formula I and the compound of Formula II to yield the compound of Formula III

DESCRIPTION OF EMBODIMENTS

The examples of present invention are described as following, but this invention is not limited by the following examples.

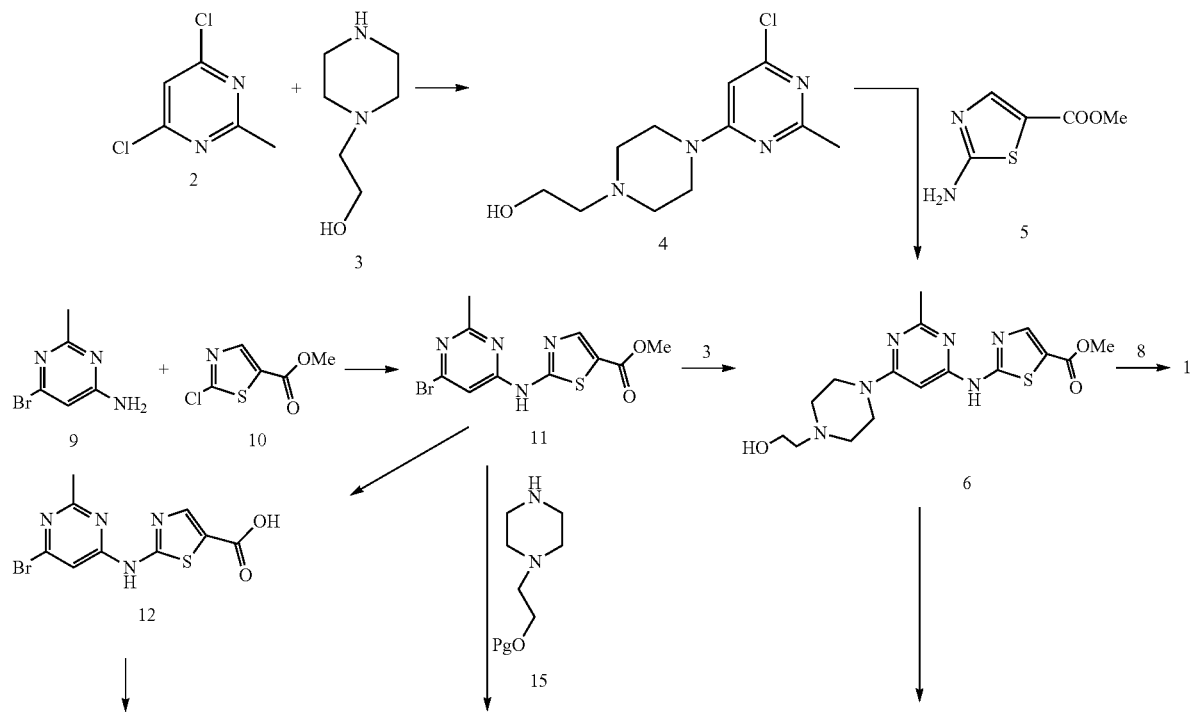

-continued

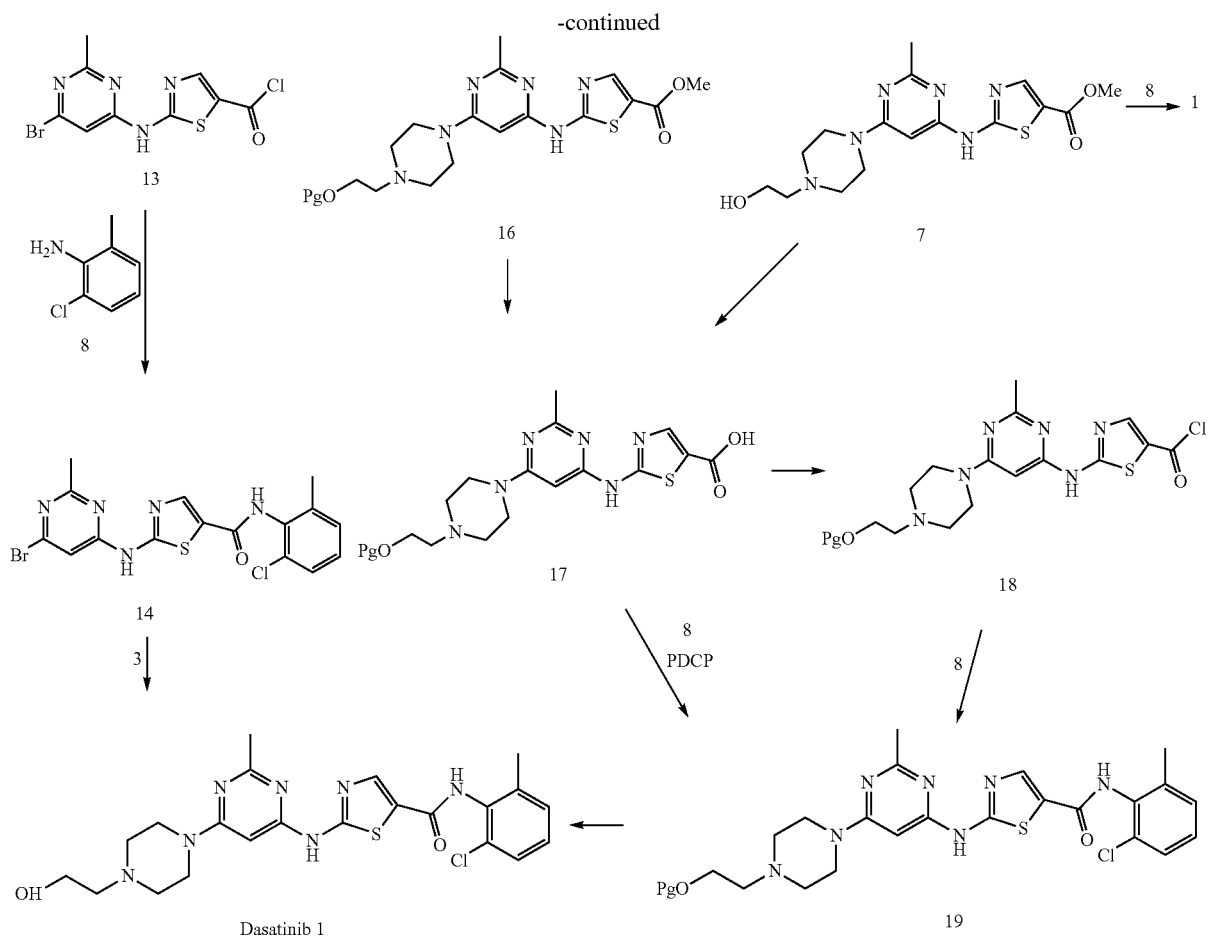

Dasatinib 1

Example 1

Synthesis of 2-(4-(6-chloro-2-methylpyrimidin-4-yl)piperazin-1-yl)ethanol (Compound 4)

1-(2-hydroxyethyl)piperazine (Compound 3) (16.6 g, 127.6 mmol)) and 2-methyl-4,6-dichloropyrimidine (Compound 2) (10.4 g, 63.8 mmol) were mixed with methylene dichloride (80 mL) in reaction flask to be stirred for 2.5 h at 30° C., and then triethylamine (1.8 mL) was added with the reaction overnight in thermal insulation. After vacuum filtration, the cake was rinsed by methylene dichloride. The filtrate was vacuum condensed to dry, and then n-hexane (40 mL) was added to grow the grains for 1 h by stirring. After vacuum filtration, the cake was rinsed by n-hexane (20 mL) and dried at 40° C. to constant weight to give white solid target Compound 4 (14.7 g, yield: 89.8%).

Element analysis: $C_{11}H_{17}ClN_4O$, Calculated: C, 51.46; H, 6.67; N, 21.82. Found: C, 51.45; H, 6.69; N, 21.82.

Example 2

Synthesis of methyl 2-(6-(4-(2-hydroxylethyl)piperazin-1-yl)-2-methylpyrimidin-4-ylamino)thiazole-5-formate (Compound 6)

2-(4-(6-chloro-2-methylpyrimidin-4-yl)piperazin-1-yl)ethanol (Compound 4) (25.7 g, 0.1 mol), methyl 2-aminothiazole-5-formate (Compound 5) (18.9 g, 0.12 mol), cesium carbonate (45.6 g, 0.14 mol), palladium acetate (2.2 g, 0.01 mol) and BINAP (6.2 g, 0.01 mol) were mixed with toluene (1100 mL) in reaction flask, and heated by stirring to reflux for 16 h. The reactant was cooled and 2 mol/L hydrochloric acid was added and stirred for 10 mins. After vacuum filtration the filtrate was phase-separated and the aqueous phase was extracted by toluene (500 mL). The separated aqueous phase was neutralized by NaOH solution (6 mol/L) at 10-15° C., and then grew the grains for 1 h. After vacuum filtration the cake was rinsed by water to give yellow solid target Compound 6 (28.5 g, yield: 75.2%).

Melting Point: 243° C.

Purity: 97.5% (HPLC, normalization method)

| HPLC Test Conditions | |
| --- | --- |
| Mobile Phase | methanol/0.05M potassium dihydrogen phosphate pH = 2.5 (55/45) |
| Detection Wavelength (λ) | 300 nm |
| Retention Time ($T_R$) | 9.598 min |

Element analysis: $C_{16}H_{22}N_6O_3S$, Calculated: C, 50.78; H, 5.86; N, 22.21. Found: C, 50.75; H, 5.87; N, 22.40.

$^1$H-NMR (500 MHz, DMSO-$d_6$): δ(ppm): 2.416-2.438 (t, 3H), 2.480-2.489 (d, 2H), 2.547-2.583 (s, 4H), 3.486-3.546 (m, 6H), 3.797 (s, 1H), 4.471 (s, 1H) (which disappeared after adding $D_2O$), 6.063 (s, 1H), 8.060 (s, 1H), 10.232 (s, 1H) (which disappeared after adding $D_2O$).

¹³C-NMR (500 MHz, DMSO-d₆): δ(ppm): 25.987, 43.955, 44.081, 51.264, 52.197, 53.162, 58.924, 60.547, 83.355, 120.180, 146.107, 157.222, 162.778, 164.276, 165.578.

ESI: (M+1): 379.23.

Employing the Above-Mentioned Synthetic Method:

Prepared from ethyl 2-aminothiazole-5-formate and Compound 4: ethyl(6-(4-(2-hydroxyethyl)piperazin-1-yl)-2-methylpyrimidin-4-ylamino)thiazole-5-formate was obtained (yield: 70.5%).

Element analysis: $C_{17}H_{24}N_6O_3S$, Calculated: C, 52.02; H, 6.16; N, 21.41. Found: C, 52.08; H, 6.15; N, 21.42.

Prepared from isopropyl 2-aminothiazole-5-formate and Compound 4: isopropyl 2-(6-(4-(2-hydroxyethyl)piperazin-1-yl)-2-methylpyrimidin-4-ylamino)thiazole-5-formate was obtained (yield: 65.2%).

Element analysis: $C_{18}H_{26}N_6O_3S$, Calculated: C, 53.18; H, 6.45; N, 20.67. Found: C, 53.15; H, 6.48; N, 20.65.

Example 3

Synthesis of 2-(6-(4-(2-hydroxylethyl)piperazin-1-yl)-2-methylpyrimidin-4-ylamino)thiazole-5-formic acid (Compound 7)

Method A

NaOH (8.0 g, 0.2 mol) was added in a reaction flask with water (190 mL) and dissolved by stirring. Then methyl 2-(6-(4-(2-hydroxyethyl)piperazin-1-yl)-2-methylpyrimidin-4-ylamino)thiazole-5-formate (Compound 6) (37.8 g, 0.1 mol) was added and stirred for reaction at room temperature overnight. The pH value of the reactant was adjusted to 6-6.5 with hydrochloric acid (6 mol/L) when the temperature is controlled between 20° C. and 25° C., and the crystal was grown by heat preservation for 2 h, and then filtrated and dried to give Compound 7 (29.6 g, yield: 81.4%).

Element analysis: $C_{15}H_{20}N_6O_3S$, Calculated: C, 49.44; H, 5.53; N, 23.06. Found: C, 49.46; H, 5.54; N, 23.03.

Employing the Above-Mentioned Synthetic Method

Prepared from ethyl(6-(4-(2-hydroxyethyl)piperazin-1-yl)-2-methylpyrimidin-4-ylamino)thiazole-5-formate: Compound 7 was obtained (yield: 75.3%).

Prepared from isopropyl 2-(6-(4-(2-hydroxyethyl)piperazin-1-yl)-2-methylpyrimidin-4-ylamino)thiazole-5-formate: Compound 7 was obtained (yield: 76.8%).

Method B

Lithium hydroxide (23.4 g, 0.35 mol) and water (265 mL) were mixed in four-necked flask and dissolved by stirring, and then methyl 2-(6-(4-(2-hydroxyethyl)piperazin-1-yl)-2-methylpyrimidin-4-ylamino)thiazole-5-formate (Compound 6) (37.8 g, 0.1 mol) was added. After reaction at 50° C. for 3 h, cooled down to room temperature and pH value was adjusted to 6-6.5 by hydrochloric acid (6N). In cold storage grew the grain overnight. After suction filtration, the cake was dried to constant weight to give target Compound 7 (35.2 g, yield: 96.7%).

Melting Point >250° C.

HPLC purity: 98.2%

| HPLC Test Conditions | |
|---|---|
| Mobile Phase | methanol/0.05M potassium dihydrogen phosphate pH = 2.5 (40/60) |
| Detection Wavelength (λ) | 300 nm |
| Retention Time ($T_R$) | 8.373 min |

Element analysis: $C_{15}H_{20}N_6O_3S$, Calculated: C, 49.44; H, 5.53; N, 23.06. Found: C, 49.43; H, 5.53; N, 23.05.

¹H-NMR (500 MHz, DMSO-d₆): δ(ppm) 2.448-2.509 (d, 3H), 3.119 (s, 2H), 3.206 (s, 2H), 3.596 (s, 2H), 3.817 (s, 4H), 4.316 (s, 2H), 5.405 (s, 1H) (which disappeared after adding D₂O), 6.197 (s, 1H), 7.978 (s, 1H), 10.962-11.759 (d, 1H) (which disappeared after adding D₂O), 12.835 (s, 1H) (which disappeared after adding D₂O).

¹³C-NMR (500 MHz, DMSO-d₆): δ(ppm) 25.939, 40.495, 41.027, 51.154, 55.561, 58.315, 84.083, 122.135, 145.401, 157.660, 162.451, 163.731, 165.847.

ESI (M+1): 365.43, (M−1): 363.42

Example 4

Synthesis of Dasatinib (Compound 1)

Method A-1:

2-(6-(4-(2-hydroxyethyl)piperazin-1-yl)-2-methylpyrimidin-4-ylamino)thiazole-5-formic acid (Compound 7) (36.4 g, 0.1 mol), THF (180 mL) and DMF (5 mL) were mixed in reaction flask, and oxalyl chloride (25.4 g, 0.2 mol) in methylene dichloride (75 mL) solution was added by droplet when the temperature is controlled between 10° C. and 20° C. After adding the mixture reacted by stirring at room temperature for 6 h and then was condensed to dry by vacuum. After that it was transferred by acetonitrile (300 mL) into a reaction flask and stirred, and 2-chloro-6-methylaniline (Compound 8) (21.3 g, 0.15 mol) in acetonitrile (500 mL) solution was added by droplet when the temperature is controlled between 10° C. and 15° C. After adding DIPEA (56 g, 0.4 mol) was completed and reacted overnight when the temperature is controlled at 30° C. After filtration the cake was rinsed by acetonitrile (100 mL) and then taken out and mixed with water (200 mL) to be washed by stirring for 30 min. Filtrated by air pump and the cake was washed by water. Then the cake was put in 80% ethanol-water solution (300 mL) and dissolved by heating. Activated carbon (1 g) was added for decolorization, and after air pump filtration the filtrate was in cold storage for crystals precipitation overnight. After air pump filtration the cake was dried to give Dasatinib (Compound 1) (28.5 g, yield: 58.4%, purity: 99.4%).

Element analysis: $C_{22}H_{26}ClN_7O_2S$, Calculated: C, 54.15; H, 5.37; N, 20.09. Found: C, 54.17; H, 5.38; N, 20.09.

Method A-2:

2-(6-(4-(2-hydroxyethyl)piperazin-1-yl)-2-methylpyrimidin-4-ylamino)thiazole-5-formic acid (Compound 7) (18.2 g, 0.05 mol), THF (90 mL) and DMF (2.5 mL) were mixed in reaction flask, and oxalyl chloride (12.7 g, 0.1 mol) in methylene dichloride (40 mL) solution was added by droplet when the temperature is controlled between 10° C. and 20° C. After adding the mixture reacted by stirring at room temperature for 6 h and then was condensed to dry by vacuum. After that it was transferred by acetonitrile (150 mL) into a reaction flask and stirred, and 2-chloro-6-methylaniline (Compound 8) (10.8 g, 0.08 mol) in acetonitrile (250 mL) solution was added by droplet when the temperature is controlled between 10° C. and 15° C. After adding DIPEA (28 g, 0.2 mol) was completed and reacted overnight when the temperature is controlled at 30° C. After filtration the cake was rinsed by acetonitrile (50 mL) and then taken out and mixed with water (100 mL) to be washed by stirring for 30 min. Filtrated by air pump and the cake was washed by water. Then it was mixed with DMSO (75 mL) and dissolved by heating to 60° C.-70° C. By the thermal insulation the mixture of water and acetone (1:1, 230 mL) was added and after crystals precipitated by stirring cooled down to 0° C. to grow the grain for 2 h. After air pump filtration the cake was rinsed by water and then by the mixture of water and acetone (1:1), and dried by air pump. With phosphorus pentoxide as an auxiliary desiccant, the cake was dried by vacuum (−0.095 MPa) at about 50° C. to give Dasatinib (Compound 1) (13.7 g, yield: 56.2%, purity: 99.92%).

Element analysis: $C_{22}H_{26}ClN_7O_2S$, Calculated: C, 54.15; H, 5.37; N, 20.09. Found: C, 54.21; H, 5.46; N, 20.13.

Method B-1: Synthesis of Dasatinib (Compound 1)

2-(6-(4-(2-hydroxyethyl)piperazin-1-yl)-2-methylpyrimidin-4-ylamino)thiazole-5-formic acid (Compound 7) (36.4 g, 0.1 mol), DMF (720 mL) and 2-chloro-6-methylaniline (Compound 8)) (17.0 mL, 0.12 mol) were mixed in a reaction flask, and when the temperature was controlled at 20° C. HATU (49.4 g, 0.13 mol) and triethylamine (25.3 mL, 0.25 mol) were added for stirred reaction overnight at room temperature. Then water (3600 mL) was added and filtrated. The cake was put in water (300 mL) for stirred wash for 30 min. After air pump filtration the cake was washed by water. Then the cake was put in 80% ethanol-water solution (600 mL) and dissolved by heating. Activated carbon (1.5 g) was added for decolorization, and after air pump filtration the filtrate was in cold storage for crystals precipitation overnight. After air pump filtration and dry, the cake was refined to give Dasatinib (Compound 1) (35.4 g, yield: 72.5%, purity: 99.7%).

Element analysis: $C_{22}H_{26}ClN_7O_2S$, Calculated: C, 54.15; H, 5.37; N, 20.09. Found: C, 54.14; H, 5.37; N, 20.07.

Method B-2: Synthesis of Dasatinib (Compound 1)

2-(6-(4-(2-hydroxyethyl)piperazin-1-yl)-2-methylpyrimidin-4-ylamino)thiazole-5-formic acid (Compound 7) (36.4 g, 0.1 mol), DMF (720 mL) and 2-chloro-6-methylaniline (Compound 8)) (17.0 mL, 0.12 mol) were mixed in a reaction flask, and when the temperature was controlled at 20° C. HATU (49.4 g, 0.13 mol) and triethylamine (25.3 mL, 0.25 mol) were added for stirred reaction overnight at room temperature. Then water (3600 mL) was added and filtrated. The cake was put in water (300 mL) for stirred wash for 30 min. After air pump filtration the cake was washed by water. Then DMSO (150 mL) was added and heated to 60° C.-70° C. After dissolving the mixture of water and ethanol (1:1, 600 mL) was added in thermal insulation. Crystals precipitated by stirring and then cooled down to 0° C. to grow the grain for 10 min. After air pump filtration the cake was rinsed by water and then by the mixture of water and ethanol (1:1), and dried by air pump. With phosphorus pentoxide as an auxiliary desiccant, the cake was dried by vacuum (−0.095 MPa) at about 50° C. to give Dasatinib (Compound 1) (38.6 g, yield: 79.1%, purity: 99.91%).

Element analysis: $C_{22}H_{26}ClN_7O_2S$, Calculated: C, 54.15; H, 5.37; N, 20.09. Found: C, 54.09; H, 5.45; N, 20.13.

Method C: Synthesis of Dasatinib (Compound 1)

Under nitrogen atmosphere, 2-(6-(4-(2-hydroxyethyl)piperazin-1-yl)-2-methylpyrimidin-4-ylamino)thiazole-5-formic acid (Compound 7) (7.3 g, 0.02 mol), PDCP (3.4 mL, 0.023 mol) and 2-chloro-6-methylaniline (Compound 8)) (2.8 mL, 0.023 mol) were added into methylene dichloride (35 mL) by stirring and cooling, and then triethylamine (8.4 mL, 0.062 mol) was added by droplets at 0° C. When finish adding it reacted by stirring at room temperature overnight. Saturated sodium bicarbonate solution was added and stirred for 15 min and then filtrated to give crude Dasatinib (Compound 1) (yield: 97.2%).

Figure 1:
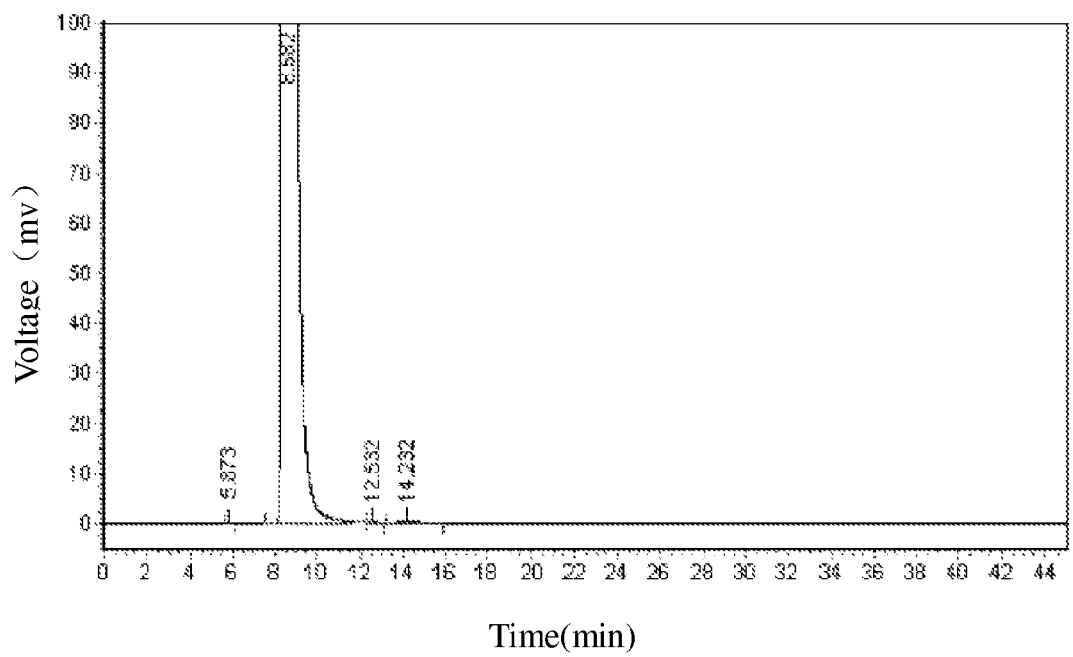
FIG. 1 is the chromatogram of Dasatinib, and the analysis result is as following.

The cake was added in DMSO (36 mL) and heated to 60° C.-70° C. by stirring. After dissolving the mixture of water and ethanol (1:1, 145 mL) was added in thermal insulation. Crystals precipitated by stirring and then cooled down to 0° C. to grow the grain for 10 min. After air pump filtration the cake was rinsed by water and then by the mixture of water and ethanol (1:1), and dried by air pump. With phosphorus pentoxide as an auxiliary desiccant, the cake was dried by vacuum (−0.095 MPa) at about 50° C. to give Dasatinib (Compound 1) (7.9 g, yield: 80.9%, purity: 99.95%, See FIG. 1)

| HPLC Test Conditions | |
|---|---|
| Mobile Phase | methanol/0.05M potassium dihydrogen phosphate pH = 2.5 (55/45) |
| Detection Wavelength (λ) | 230 nm |
| Retention Time ($T_R$) | 8.582 min |

$^1$H-NMR (500 MHz, DMSO-$d_6$): δ(ppm) 2.245 (s, 3H), 2.413-2.446 (s, 5H), 2.491-2.509 (m, 4H), 3.521-3.557 (q, 6H), 4.46 (s, 1H), 6.05 (s, 1H), 7.248-7.305 (m, 3H), 8.226 (s, 1H), 9.883 (s, 1H), 11.476 (s, 1H).

$^1$H-NMR (500 MHz, DMSO-$d_6$, $D_2O$): δ(ppm) 2.233 (s, 3H), 2.403-2.435, (s, 5H), 2.473-2.507 (d, 4H), 6.047 (s, 1H), 7.238-7.292 (m, 2H), 7.386-7.400 (d, 1H), 8.218 (s, 1H).

$^{13}$C-NMR (500 MHz, DMSO-$d_6$): δ(ppm) 18.756, 26.034, 44.098, 53.186, 58.997, 60.658, 83.098, 126.157, 127.458, 128.612, 129.474, 132.910, 134.002, 139.285, 141.286, 157.410, 160.393, 162.964, 165.629.

ESI (M+1): 490.27

Example 5

Synthesis of methyl 2-(6-bromo-2-methylpyrimidin-4-ylamino)thiazole-5-formate (Compound 11)

60% sodium hydride (12.0 g, 0.30 mol) was suspended in THF (300 mL) and cooled down to 0° C. 4-amino-6-bromo-2-methylpyrimidine (Compound 9) (18.7 g, 0.1 mol) was then added in batches and stirred for 30 min. After methyl 2-chlorothiazole-5-formate (Compound 10) (17.7 g, 0.1 mol) was added in batches, the reactants were heated and reacted by refluxing for 4 h, and then cooled down to room temperature for reaction overnight. When controlling the temperature between 0° C. and 5° C., hydrochloric acid (2N) was added for neutralization reaction. After adding keep heat and stirred to grow grains for 1 h. Filtrate and wash the cake with water, and then dry to give target Compound 11 (25.8 g, yield is 78.4%).

Element analysis: $C_{10}H_9BrN_4O_2S$, Calculated: C, 36.49; H, 2.76; N, 17.02. Found: C, 36.51; H, 2.77; N, 16.99.

$^1$H-NMR (500 MHz, DMSO-$d_6$): δ(ppm) 2.580 (s, 3H), 3.820 (s, 3H), 6.960 (S, 1H), 8.160 (s, 1H), 12.376 (s, 1H) (which disappeared after exchanging $D_2O$)

$^{13}$C-NMR (500 MHz, DMSO-$d_6$): δ(ppm) 25.700, 52.800, 104.161, 121.662, 146.010, 157.910, 159.124, 162.412, 162.949, 167.871.

Employing the Above-Mentioned Synthetic Method

Prepared from ethyl 2-chlorothiazole-5-formate and Compound 9: ethyl 2-(6-bromo-2-methylpyrimidin-4-ylamino) thiazole-5-formate was yielded (yield: 75.5%).

Element analysis: $C_{11}H_{11}BrN_4O_2S$, Calculated: C, 38.50; H, 3.23; N, 16.32. Found: C, 38.62; H, 3.21; N, 16.30.

Prepared from isopropyl 2-chlorothiazole-5-formate and Compound 9: isopropyl 2-(6-bromo-2-methylpyrimidin-4-ylamino)thiazole-5-formate was yielded (yield: 76.9%).

Element analysis: $C_{12}H_{13}BrN_4O_2S$, Calculated: C, 40.35; H, 3.67; N, 15.68. Found: C, 40.37; H, 3.66; N, 15.70.

Example 6

Synthesis of methyl 2-(6-(4-(2-hydroxyethyl)piperazin-1-yl)-2-methylpyrimidin-4-ylamino)thiazole-5-formate (Compound 6)

1-(2-hydroxyethyl)piperazine (Compound 3) (65 g, 0.5 mol), methyl 2-(6-bromo-2-methylpyrimidin-4-ylamino)thiazole-5-formate (Compound 11) (32.9 g, 0.1 mol), n-butanol (280 mL) and DIPEA (28.3 g, 0.2 mol) were mixed in reaction flask and reacted by refluxing for 8 h. Cooled down to room temperature and crystals precipitated overnight. After air pump filtration the cake was rinsed by n-butanol and dried to give target Compound 6 (31.7 g, yield: 83.8%).

Melting Point: 242.5° C.

Element analysis: $C_{16}H_{22}N_6O_3S$, Calculated: C, 50.78; H, 5.86; N, 22.21. Found: C, 50.76; H, 5.86; N, 22.22.

Employing the Above-Mentioned Synthetic Method:

Prepared from ethyl 2-(6-bromo-2-methylpyrimidin-4-ylamino)thiazole-5-formate and Compound 3: ethyl 2-(6-(4-(2-hydroxyethyl)piperazin-1-yl)-2-methylpyrimidin-4-ylamino)thiazole-5-formate was yielded (yield: 80.6%).

Element analysis: $C_{17}H_{24}N_6O_3S$, Calculated: C, 52.02; H, 6.16; N, 21.41. Found: C, 52.08; H, 6.14; N, 21.41.

Prepared from isopropyl 2-(6-bromo-2-methylpyrimidin-4-ylamino)thiazole-5-formate and Compound 3: isopropyl 2-(6-(4-(2-hydroxyethyl)piperazin-1-yl)-2-methylpyrimidin-4-ylamino)thiazole-5-formate was yielded (yield: 77.2%).

Element analysis: $C_{18}H_{26}N_6O_3S$, Calculated: C, 53.18; H, 6.45; N, 20.67. Found: C, 53.21; H, 6.45; N, 20.64.

Example 7

Synthesis of 2-(6-bromo-2-methylpyrimidin-4-ylamino)thiazole-5-formic acid (Compound 12)

Methyl 2-(6-bromo-2-methylpyrimidin-4-ylamino)thiazole-5-formate (Compound 11) (32.9 g, 0.1 mol) was added into a solution of NaOH (8.0 g, 0.2 mol) in water (250 mL) prepared in advance, and reacted by stirring at room temperature overnight. After filtration the filtrate was transferred into reaction flask and pH value was adjusted to 6-6.5 with hydrochloric acid (6N) when the temperature is controlled between 20° C. and 25° C. Grew the grain by stirring for 2 h, and then filtrated and dried to give Compound 12 (21.2 g, yield: 78.3%).

Element analysis: $C_9H_7BrN_4O_2S$, Calculated: C, 34.30; H, 2.24; N, 17.78. Found: C, 34.26; H, 2.27; N, 17.77.

Employing the Above-Mentioned Synthetic Method:

Prepared from ethyl 2-(6-(4-(2-hydroxyethyl)piperazin-1-yl)-2-methylpyrimidin-4-ylamino)thiazole-5-formate: Compound 12 was yielded (yield: 81.5%).

Element analysis: $C_9H_7BrN_4O_2S$, Calculated: C, 34.30; H, 2.24; N, 17.78. Found: C, 34.32; H, 2.24; N, 17.77.

Prepared from isopropyl 2-(6-(4-(2-hydroxyethyl)piperazin-1-yl)-2-methylpyrimidin-4-ylamino)thiazole-5-formate: Compound 12 was yielded (yield: 76.3%).

Element analysis: $C_9H_7BrN_4O_2S$, Calculated: C, 34.30; H, 2.24; N, 17.78. Found: C, 34.29; H, 2.24; N, 17.78.

Example 8

Synthesis of 2-(6-bromo-2-methylpyrimidin-4-ylamino)-N-(2-chloro-6-methylphenyl)thiazole-5-formamide (Compound 14)

Method A 2-(6-bromo-2-methylpyrimidin-4-ylamino)thiazole-5-formic acid (Compound 12) (31.5 g, 0.1 mol), THF (315 mL) and DMF (3 mL) were mixed in reaction flask, and a solution of oxalyl chloride (25.4 g, 0.2 mol) in methylene dichloride (100 mL) was added by droplet when the temperature is controlled between 10° C. and 20° C. After adding, the mixture reacted by stirring at room temperature for 5 h and then was condensed to dry by vacuum to yield 2-(6-bromo-2-methylpyrimidin-4-ylamino)thiazole-5-formyl chloride (Compound 13), which was transferred by acetonitrile (500 mL) into reaction flask. a solution of 2-chloro-6-methylaniline (Compound 8) (21.2 g, 0.15 mol) in acetonitrile (500 mL) was added by droplet and stirred when the temperature is controlled between 10° C. and 15° C. After adding, DIPEA (56 g, 0.4 mol) was added and reacted overnight when the temperature is controlled at 30° C. When Cooled down to 0-5° C., hydrochloric acid (1N, 1000 mL) was added and stirred for 1 h. After filtration, the cake was washed by water and then dried to give target Compound 14 (23.3 g, yield: 53.2%).

Element analysis: $C_{16}H_{13}BrClN_5OS$, Calculated: C, 43.80; H, 2.99; N, 15.96. Found: C, 43.83; H, 2.96; N, 15.97.

Method B:

2-(6-bromo-2-methylpyrimidin-4-ylamino)thiazole-5-formic acid (Compound 12) (31.5 g, 0.1 mol), DMF (630 mL) and 2-chloro-6-methylaniline (Compound 8) (17.0 g, 0.12 mol) were mixed in a reaction flask, and then HATU (45.6 g, 0.2 mol) and triethylamine (25.3 g, 0.25 mol) was added when controlling the temperature at 20° C. Then the mixture reacted by stirring at room temperature overnight. After that water (3150 mL) was added and stirred for 30 min and then filtrated. The cake was dried to give target Compound 14 (31.2 g, yield: 71.1%).

Element analysis: $C_{16}H_{13}BrClN_5OS$, Calculated: C, 43.80; H, 2.99; N, 15.96. Found: C, 43.86; H, 2.95; N, 15.98.

Method C:

Under nitrogen atmosphere, 2-(6-bromo-2-methylpyrimidin-4-ylamino)thiazole-5-formic acid (Compound 12) (15.8 g, 0.05 mol), PDCP (9.0 mL, 0.06 mol) and 2-chloro-6-methylaniline (Compound 8)) (7.4 mL, 0.06 mol) were added into methylene dichloride (650 mL) by stirring and cooling, and then triethylamine (20.4 mL, 0.15 mol) was added by droplets at 0° C. When finish adding, it reacted by stirring at room temperature overnight. Saturated sodium bicarbonate aqueous solution was added and stirred for 15 mins and then filtrated. The cake was taken up and added in DMSO (80 mL) and heated to 60° C.-70° C. when stirring. After dissolving, the mixture of water and ethanol (1:1, 320 mL) was added in thermal insulation. Crystals precipitated by stirring and then cooled down to 0° C. to grow the grain for 1 h. After air pump filtration the cake was rinsed by water and then by the mixture of water and ethanol (1:1), and dried by air pump. With phosphorus pentoxide as an auxiliary desiccant, the cake was dried by vacuum (−0.095 MPa) at about 50° C. to give Compound 14 (17.0 g, yield: 77.5%).

Example 9

Synthesis of Dasatinib (Compound 1)

Method A:

1-(2-hydroxyethyl)piperazine (Compound 3) (65 g, 0.5 mol), 2-(6-bromo-2-methylpyrimidin-4-ylamino)-N-(2-chloro-6-methylphenyl)thiazole-5-formamide (Compound 14) (43.9 g, 0.1 mol), n-butanol (670 mL) and DIPEA (28.3 g, 0.2 mol) were mixed in reaction flask and reacted by refluxing for 7 h. After the reactant was cooled down to room temperature, crystals precipitated overnight. After air pump filtration, the cake was rinsed with n-butanol (500 mL) by stirring for 30 min. Then filtrated and the cake was dried to give white solid target Compound 1 (42.9 g, yield: 87.9%).

Element analysis: $C_{22}H_{26}ClN_7O_2S$, Calculated: C, 54.15; H, 5.37; N, 20.09. Found: C, 54.15; H, 5.39; N, 20.06.

Method B:

1-(2-hydroxyethyl)piperazine (Compound 3) (65 g, 0.5 mol), 2-(6-bromo-2-methylpyrimidin-4-ylamino)-N-(2-chloro-6-methylphenyl)thiazole-5-formamide (Compound 14) (43.9 g, 0.1 mol), isopropanol (650 mL) and DIPEA (28.3 g, 0.2 mol) were mixed in reaction flask and reacted by refluxing for 5 h. It was condensed by vacuum to dry to give crude Dasatinib (Compound 1) (purity: 95.4%).

Crude Dasatinib (Compound 1) was added into DMF (180 mL) and dissolved by heating to 60° C. By the thermal insulation the mixture of water and acetone (1:1, 540 mL) was added and after crystals precipitated by stirring cooled down to 0° C. to grow the grain for 1.5 h. After air pump filtration the cake was rinsed by water and then by the mixture of water and acetone (1:1), and dried by air pump. With phosphorus pentoxide as an auxiliary desiccant, the cake was dried by vacuum (−0.095 MPa) at about 50° C. to give white solid target Compound 1 (35.9 g, yield: 73.6%, purity: 99.56%).

Element analysis: $C_{22}H_{26}ClN_7O_2S$, Calculated: C, 54.15; H, 5.37; N, 20.09. Found: C, 54.19; H, 5.42; N, 20.00.

$^1$H-NMR (500 MHz, DMSO-$d_6$): δ(ppm) 2.243 (s, 3H), 2.411-2.446 (d, 5H), 2.494-2.500 (d, 4H), 3.396-3.523 (q, 6H), 4.333-4.456 (q, 1H), 6.047 (s, 1H), 7.252-7.304 (t, 2H), 7.398-7.414 (d, 1H), 8.217 (s, 1H), 9.875 (s, 1H), 11.467 (s, 1H).

ESI (M+1): 490.33

Example 10

Synthesis of methyl 2-(6-(4-(2-benzyloxyethyl)piperazin-1-yl)-2-methylpyrimidin-4-ylamino)thiazole-5-formate (Compound 16, Pg is benzyl)

Methyl 2-(6-bromo-2-methylpyrimidin-4-ylamino) thiazol-5-formate (Compound 11) (5.46 g, 0.017 mol), benzyloxyethyl piperazine (Compound 15, Pg is benzyl) (11 g, 0.05 mol) and n-butanol (50 mL) were mixed in a four-necked flask. With stirring DIPEA (5.5 mL) was added and reacted for 4 h by heating to refluxing temperature. After reaction grew the grain overnight at room temperature. Air pump filtrated and the cake was rinsed by proper amount of frozen n-butanol. Then it was dried to constant weight by blast at 60° C. to give yellow solid target Compound 16 (Pg is benzyl) (4.95 g, yield: 63.7%).

Element analysis: $C_{23}H_{28}N_6O_3S$, Calculated: C, 58.95; H, 6.02; N, 17.94. Found: C, 58.84; H, 6.11; N, 17.91.

Employing the Above-Mentioned Synthetic Method:

Prepared from 4-methoxybenzyloxyethyl piperazine: methyl 2-(6-(4-(2-(4-methoxybenzyloxyethyl)) piperazin-1-yl)-2-methylpyrimidin-4-ylamino) thiazol-5-formate was yielded (Compound 16, Pg is 4-methoxybenzyl) (yield: 59.7%).

Element analysis: $C_{24}H_{30}N_6O_4S$, Calculated: C, 57.81; H, 6.06; N, 16.86. Found: C, 57.76; H, 6.13; N, 16.79.

Prepared from methoxymethyloxyethyl piperazine: methyl 2-(6-(4-(2-methoxymethyloxyethyl)piperazin-1-yl)-2-methylpyrimidin-4-yl amino) thiazol-5-formate was yielded (Compound 16, Pg is methoxymethyl) (yield: 61.2%).

Element analysis: $C_{18}H_{26}N_6O_4S$, Calculated: C, 51.17; H, 6.20; N, 19.89. Found: C, 51.11; H, 6.31; N, 19.92.

Prepared from ethoxyethyloxyethyl piperazine: methyl 2-(6-(4-(2-ethoxyethyloxyethyl)piperazin-1-yl)-2-methylpyrimidin-4-ylamino)thiazol-5-formate was yielded (Compound 16, Pg is ethoxyethyl) (yield: 55.2%).

Element analysis: $C_{20}H_{30}N_6O_4S$, Calculated: C, 53.32; H, 6.71; N, 18.65. Found: C, 53.25; H, 6.84; N, 18.61.

Prepared from methylthiomethyloxyethyl piperazine: methyl 2-(6-(4-(2-methylthiomethyloxyethyl)piperazin-1-yl)-2-methylpyrimidin-4-ylamino)thiazol-5-formate was yielded (Compound 16, Pg is methylthiomethyl) (yield: 50.3%).

Element analysis: $C_{18}H_{26}N_6O_3S_2$, Calculated: C, 49.30; H, 5.98; N, 19.16. Found: C, 49.37; H, 6.04; N, 19.11.

Example 11

Synthesis of 2-(6-(4-(2-benzyloxyethyl)piperazin-1-yl)-2-methylpyrimidin-4-ylamino)thiazole-5-formic acid (Compound 17, Pg is benzyl)

Sodium hydroxide (1.27 g, 0.032 mol) and water (25 mL) were mixed in four-necked flask, and methyl 2-(6-(4-(2-benzyloxyethyl)piperazin-1-yl)-2-methylpyrimidin-4-ylamino) thiazole-5-formate (Compound 16, Pg is benzyl) (4.95 g, 0.011 mol) was added below 60° C. Then heated to 80° C. and reacted for 4 h. After reaction, cooled down to room temperature and pH value was adjusted to 2 by hydrochloric acid (6N). Grew the grain at room temperature overnight. After air pump filtration, the cake was dried to constant weight by blast at 60° C. to give light yellow solid target Compound 17 (Pg is benzyl) (4.7 g, yield: 97.9%)

Element analysis: $C_{22}H_{26}N_6O_3S$, Calculated: C, 58.13; H, 5.77; N, 18.49. Found: C, 58.18; H, 5.83; N, 18.43.

Employing the Above-Mentioned Synthetic Method:

Prepared from methyl 2-(6-(4-(2-(4-methoxybenzyloxyethyl)) piperazin-1-yl)-2-methylpyrimidin-4-ylamino) thiazol-5-formate (Compound 16, Pg is 4-methoxybenzyl): 2-(6-(4-(2-(4-methoxybenzyloxyethyl)) piperazin-1-yl)-2-methylpyrimidin-4-ylamino)thiazole-5-formic acid (Compound 17, Pg is 4-methoxybenzyl) was yielded (yield: 92.2%).

Element analysis: $C_{23}H_{28}N_6O_4S$, Calculated: C, 57.01; H, 5.82; N, 17.34. Found: C, 57.10; H, 5.90; N, 17.30.

Prepared from methyl 2-(6-(4-(2-methoxymethyloxyethyl)) piperazin-1-yl)-2-methylpyrimidin-4-ylamino) thiazol-5-formate (Compound 16, Pg is methoxymethyl): 2-(6-(4-(2-methoxymethyloxyethyl)piperazin-1-yl)-2-methylpyrimidin-4-ylamino)thiazole-5-formic acid (Compound 17, Pg is methoxymethyl) was yielded (yield: 94.7%).

Element analysis: $C_{17}H_{24}N_6O_4S$, Calculated: C, 49.99; H, 5.92; N, 20.57. Found: C, 50.03; H, 5.99; N, 20.61.

Prepared from methyl 2-(6-(4-(2-ethoxyethyloxyethyl)) piperazin-1-yl)-2-methylpyrimidin-4-ylamino)thiazol-5-formate (Compound 16, Pg is ethoxyethyl): 2-(6-(4-(2- ethoxyethyloxyethyl)piperazin-1-yl)-2-methylpyrimidin-4-ylamino)thiazole-5-formic acid (Compound 17, Pg is ethoxyethyl) was yielded (yield: 95.2%).

Element analysis: $C_{19}H_{28}N_6O_4S$, Calculated: C, 52.28; H, 6.47; N, 19.25. Found: C, 52.25; H, 6.43; N, 19.21.

Prepared from methyl 2-(6-(4-(2-methylthiomethyloxyethyl)) piperazin-1-yl)-2-methylpyrimidin-4-ylamino)thiazol-5-formate (Compound 16, Pg is methylthiomethyl): 2-(6-(4-(2-methylthiomethyloxyethyl)piperazin-1-yl)-2-methylpyrimidin-4-ylamino)thiazole-5-formic acid (Compound 17, Pg is methylthiomethyl) was yielded (yield: 92.2%).

Element analysis: $C_{17}H_{24}N_6O_3S_2$, Calculated: C, 48.09; H, 5.70; N, 19.80. Found: C, 48.13; H, 5.79; N, 19.77.

Example 12

Synthesis of benzyl-protected Dasatinib (Compound 19, Pg is benzyl)

Under nitrogen atmosphere, 2-(6-(4-(2-benzyloxyethyl)piperazin-1-yl)-2-methylpyrimidin-4-ylamino)thiazole-5-formic acid (Compound 17, Pg is benzyl) (13.6 g, 0.03 mol), PDCP (5.4 mL, 0.036 mol) and 2-chloro-6-methylaniline (Compound 8)) (4.4 mL, 0.036 mol) were added into methylene dichloride (55 mL) by stirring, and then cooling down to 0° C., triethylamine (12.3 mL, 0.09 mol) was added by droplets. When finish adding, it reacted by stirring at room temperature overnight. Saturated sodium bicarbonate aqueous solution was added and stirred for 10 mins and then filtrated. The cake was dried to constant weight by blast at 60° C. to give target Compound 19 (Pg is benzyl) (11.2 g, yield: 64.7%).

Element analysis: $C_{29}H_{32}ClN_7O_2S$, Calculated: C, 60.25; H, 5.58; N, 16.96. Found: C, 60.21; H, 5.51; N, 16.92.

Employing the Above-Mentioned Synthetic Method:

Prepared from 2-(6-(4-(2-(4-methoxybenzyloxyethyl))piperazin-1-yl)-2-methylpyrimidin-4-ylamino)thiazole-5-formic acid (Compound 17, Pg is 4-methoxybenzyl): 4-methoxybenzyl-protected Dasatinib was yielded (Compound 19, Pg is 4-methoxybenzyl (yield: 59.1%).

Element analysis: $C_{30}H_{34}ClN_7O_3S$, Calculated: C, 59.25; H, 5.64; N, 16.12. Found: C, 59.21; H, 5.70; N, 16.18.

Prepared from 2-(6-(4-(2-methoxymethyloxyethyl)piperazin-1-yl)-2-methylpyrimidin-4-ylamino)thiazole-5-formic acid (Compound 17, Pg is methoxymethyl): methoxymethyl-protected Dasatinib was yielded (Compound 19, Pg is methoxymethyl (yield: 66.4%).

Element analysis: $C_{24}H_{30}ClN_7O_3S$, Calculated: C, 54.18; H, 5.68; N, 18.43. Found: C, 54.22; H, 5.71; N, 18.40.

Prepared from 2-(6-(4-(2-ethoxyethyloxyethyl)piperazin-1-yl)-2-methylpyrimidin-4-ylamino)thiazole-5-formic acid (Compound 17, Pg is ethoxyethyl): ethoxyethyl-protected Dasatinib was yielded (Compound 19, Pg is ethoxyethyl (yield: 48.6%).

Element analysis: $C_{26}H_{34}ClN_7O_3S$, Calculated: C, 55.75; H, 6.12; N, 17.50. Found: C, 55.71; H, 6.19; N, 17.54.

Prepared from 2-(6-(4-(2-methylthiomethyloxyethyl)piperazin-1-yl)-2-methylpyrimidin-4-ylamino)thiazole-5-formic acid (Compound 17, Pg is methylthiomethyl): methylthiomethyl-protected Dasatinib was yielded (Compound 19, Pg is methylthiomethyl (yield: 59.5%).

Element analysis: $C_{24}H_{30}ClN_7O_2S_2$, Calculated: C, 52.59; H, 5.52; N, 17.89. Found: C, 52.61; H, 5.60; N, 17.83.

Example 13

Synthesis of Dasatinib (Compound 1)

Benzyl-protected Dasatinib (Compound 19, Pg is benzyl) (5.8 g, 0.01 mol) was added into anhydrous methylene dichloride (20 mL), and when the mixture was cooled down to −15° C., a solution of boron trichloride (1M) in methylene dichloride (60 mL, 0.06 mol) was added by droplet. After adding, reacted in thermal insulation with stirring for 5 h and then at room temperature overnight. The reactant was added into icy water slowly and filtrated by air pump to give crude Dasatinib (Compound 1) (purity: 98.3%). The cake was put into DMSO (20 mL) directly and heated to 60-70° C. by stirring. After dissolution the mixture of water and ethanol (1:1, 80 mL) was added in thermal insulation. By stirring crystal was precipitated and then grew the grain for 10 min when cooling down to 0° C. After air pump filtration, the cake was rinsed by water and then by the mixture of water and ethanol (1:1), and dried by air pump. With phosphorus pentoxide as an auxiliary desiccant, the cake was dried by vacuum (−0.095 MPa) at about 50° C. to give Dasatinib (Compound 1) (4.01 g, yield: 82.2%, purity: 99.92%).

Employing the Above-Mentioned Synthetic Method:

Prepared from 4-methoxybenzyl-protected Dasatinib (Compound 19, Pg is 4-methoxybenzyl): Dasatinib (Compound 1) was yielded (yield: 77.3%, purity: 99.72%).

Prepared from methoxymethyl-protected Dasatinib (Compound 19, Pg is methoxymethyl): Dasatinib (Compound 1) was yielded (yield: 70.6%, purity: 99.80%).

Prepared from ethoxyethyl-protected Dasatinib (Compound 19, Pg is ethoxyethyl): Dasatinib (Compound 1) was yielded (yield: 72.5%, purity: 99.53%).

Prepared from methylthiomethyl-protected Dasatinib (Compound 19, Pg is methylthiomethyl): Dasatinib (Compound 1) was yielded (yield: 80.7%, purity: 99.61%).

Example 14

Synthesis of 2-(6-(4-(2-acetoxyethyl)piperazin-1-yl)-2-methylpyrimidin-4-ylamino)thiazole-5-formic acid (Compound 17, Pg is acetoxyethyl)

2-(6-(4-(2-hydroxyethyl)piperazin-1-yl)-2-methylpyrimidin-4-ylamino)thiazole-5-formic acid (Compound 7) (30 g, 0.082 mol), pyridine (300 mL) and DMAP (0.3 g) were mixed in a four-necked flask, and acetic anhydride was added by droplet when the temperature was controlled at 30° C. After adding, it was heated up to 50° C. and reacted overnight in thermal insulation. After reaction it was cooled down to room temperature and grew the grain overnight. After air pump filtration, the cake was rinsed by suitable amount of methylene dichloride. Then the cake was taken up and put into methylene dichloride (150 mL) and stirred for 30 min at room temperature. After air pump filtration the cake was dried to constant weight by blast at 60° C. to give light yellow to off-white solid target Compound 17 (Pg is acetyl) (24 g, yield: 71.7%).

Melting Point: 241° C.
Purity: 98.3% (HPLC, normalization method)

| HPLC Test Conditions | |
| --- | --- |
| Mobile Phase | methanol/0.05M potassium dihydrogen phosphate pH = 2.5 (40/60) |

-continued

| HPLC Test Conditions | |
|---|---|
| Detection Wavelength (λ) | 300 nm |
| Retention Time ($T_R$) | 10.507 min |

Element analysis: $C_{17}H_{22}N_6O_4S$, Calculated: C, 50.23; H, 5.46; N, 20.68. Found: C, 50.25; H, 5.48; N, 20.62.

$^1$H-NMR (500 MHz, DMSO-$d_6$): δ(ppm) 2.093 (s, 3H), 2.455 (s, 3H), 2.548 (s, 4H), 3.118-3.214 (d, 4H), 3.591 (s, 2H), 4.340 (s, 2H), 6.165 (s, 1H), 7.984 (s, 1H), 11.312-11.736 (d, 1H) (which disappeared after adding $D_2O$), 12.824 (s, 1H) (which disappeared after adding $D_2O$).

$^{13}$C-NMR (500 MHz, DMSO-$d_6$): δ(ppm) 21.262, 25.943, 40.916, 41.092, 51.096, 54.578, 58.671, 84.015, 122.143, 145.407, 157.651, 162.424, 163.743, 165.864, 170.532.

ESI: (M+1): 406.48, M: 405.47.

Employing the Above-Mentioned Synthetic Method:
Prepared from benzoic acid anhydride: 2-(6-(4-(2-benzoyloxyethyl)piperazin-1-yl)-2-methylpyrimidin-4-ylamino)thiazole-5-formic acid (Compound 17, Pg is benzoyl) was obtained (yield: 74.2%).

Element analysis: $C_{22}H_{24}N_6O_4S$, Calculated: C, 56.40; H, 5.16; N, 17.94. Found: C, 56.45; H, 5.11; N, 17.92.

Example 15

Synthesis of Dasatinib protected by acetyl (Compound 19, Pg is acetyl)

Method A:
2-(6-(4-(2-acetoxyethyl)piperazin-1-yl)-2-methylpyrimidin-4-ylamino)thiazole-5-formic acid (Compound 17, Pg is acetyl) (30 g, 0.074 mol), methylene dichloride (270 mL) and DMF (3 mL) were mixed in a four-necked flask and cooled down. Then a solution of oxalyl chloride (12.7 mL) in methylene dichloride (30 mL) was added by droplet when the temperature is controlled between 0° C. and 5° C. After adding, the mixture was heated and reacted at room temperature for 3 h. Filtrated and the cake was mixed with methylene dichloride (300 mL) in reaction flask, and cooled down to 0° C. by stirring. 2-chloro-6-methylaniline (Compound 8) (13.6 mL, 0.11 mol) was added, as well as a solution of DIPEA (21 mL, 0.12 mol) in methylene dichloride (30 mL) was added by droplet. After adding, it reacted at room temperature for 2 h. After reaction saturated sodium bicarbonate solution was added and stirred for 30 mins. Filtrated and the cake was dried to constant weight at 60° C. by blast to give target Compound 19 (Pg is acetyl) (yield: 40.8%).

Melting Point: 295.2° C.
Purity: 98.5% (HPLC, normalization method)

| HPLC Test Conditions | |
|---|---|
| Mobile Phase | methanol/0.05M potassium dihydrogen phosphate pH = 2.5 (55/45) |
| Detection Wavelength (λ) | 300 nm |
| Retention Time ($T_R$) | 12.315 min |

Element analysis: $C_{24}H_{28}ClN_7O_3S$, Calculated: C, 54.38; H, 5.32; N, 18.50. Found: C, 54.42; H, 5.40; N, 18.55.

$^1$H-NMR (500 MHz, DMSO-$d_6$): δ(ppm) 2.030 (s, 3H), 2.245 (s, 3H), 2.372-2.414 (d, 3H), 2.584-2.605 (t, 6H), 3.517 (s, 4H), 4.133-4.155 (t, 2H), 6.056 (s, 1H), 7.248-7.305 (m, 2H), 7.400-7.414 (t, 1H), 8.226 (s, 1H), 9.883 (s, 1H), 11.845 (s, 1H).

$^1$H-NMR (500 MHz, DMSO-$d_6$, $D_2O$): δ(ppm) 2.020-2.055 (d, 3H), 2.240-2.278 (d, 3H), 2.367-2.441 (t, 3H), 2.491-2.501 (d, 4H), 2.546-2.592 (q, 2H), 3.423 (s, 1H), 3.514 (s, 1H), 4.122-4.144 (t, 1H), 6.054 (s, 1H), 7.240-7.296 (m, 2H), 7.391-7.406 (d, 1H), 8.230 (m, 1H).

$^{13}$C-NMR (500 MHz, DMSO-$d_6$): δ(ppm) 18.759, 21.237, 26.034, 44.053, 52.866, 56.480, 61.695, 83.198, 126.080, 127.458, 128.594, 129.473, 132.921, 134.036, 139.297, 141.320, 157.532, 160.411, 163.001, 165.617, 170.780.

ESI: (M) 531.29

Employing the Above-Mentioned Synthetic Method:
Prepared from 2-(6-(4-(2-benzoyloxyethyl)piperazin-1-yl)-2-methylpyrimidin-4-ylamino)thiazole-5-formic acid (Compound 17, Pg is benzoyl): Dasatinib protected by benzoyl group was obtained (Compound 19) (yield: 43.1%).

Element analysis: $C_{29}H_{30}ClN_7O_3S$, Calculated: C, 58.83; H, 5.11; N, 16.56. Found: C, 58.89; H, 5.19; N, 16.58.

Method B:
Under nitrogen atmosphere, 2-(6-(4-(2-acetyloxyethyl)piperazin-1-yl)-2-methylpyrimidin-4-ylamino)thiazole-5-formic acid (Compound 17, Pg is acetyl) (8.5 g, 0.021 mol), PDCP (3.4 mL, 0.023 mol) and 2-chloro-6-methylaniline (Compound 8) (2.8 mL, 0.023 mol) were added into methylene dichloride (34 mL) by stirring, and then when cooling down to 0° C. triethylamine (8.4 mL, 0.062 mol) was added by droplets. After adding, it reacted by stirring at room temperature overnight. Saturated sodium bicarbonate aqueous solution was added and stirred for 10 mins and then filtrated. The cake was dried to constant weight by blast at 60° C. to give light yellow to off-white solid target Compound 19 (Pg is acetyl) (7.98 g, yield: 71.7%).

Melting Point: 295.5° C.
Element analysis: $C_{24}H_{28}ClN_7O_3S$, Calculated: C, 54.38; H, 5.32; N, 18.50. Found: C, 54.32; H, 5.38; N, 18.57.

Employing the Above-Mentioned Synthetic Method:
Prepared from 2-(6-(4-(2-benzoyloxyethyl)piperazin-1-yl)-2-methylpyrimidin-4-ylamino)thiazole-5-formic acid (Compound 17, Pg is benzoyl): Dasatinib protected by benzoyl group was yielded: Compound 19 (Pg is benzoyl) (yield: 76.3%).

Element analysis: $C_{29}H_{30}ClN_7O_3S$, Calculated: C, 58.83; H, 5.11; N, 16.56. Found: C, 58.87; H, 5.19; N, 16.61.

Example 16

Synthesis of Dasatinib (Compound 1)

Sodium hydroxide (9.5 g, 0.24 mol), water (150 mL) and acetyl-protected Dasatinib (Compound 19, Pg is acetyl) were mixed in four-necked flask and reacted for 2 h at 50° C. in thermal insulation. Then cooled down to below 25° C. and pH value was adjusted to 4 by hydrochloric acid (6N). Grew the grain at room temperature overnight. After air pump filtration, crude Dasatinib (Compound 1) was yielded (purity: 97.6%), which was added into DMSO (100 mL) and dissolved under stirring by heating to 60-70° C. By the thermal insulation, the mixture of water and ethanol (1:1, 400 mL) was added and after crystals precipitated by stirring cooled down to 0° C. to grow the grain for 2 h. After air pump filtration, the cake was rinsed by water and then by the mixture of water and ethanol (1:1), and dried by air pump. With phosphorus pentoxide as an auxiliary desiccant, the cake was dried by vacuum (−0.095 MPa) at about 50° C. to give Dasatinib (24.5 g, yield: 88.7%, purity: 99.93%).

$^1$H-NMR (500 MHz, DMSO-d$_6$): δ (ppm) 2.243 (s, 3H), 2.411-2.440 (s, 3H), 2.484-2.507 (d, 4H), 3.513-3.554 (q, 6H), 4.443-4.464 (t, 1H), 6.052 (s, 1H), 7.246-7.304 (m, 2H), 7.398-7.413 (d, 1H), 8.223 (s, 1H), 9.881 (s, 1H), 11.474 (s, 1H).

Employing the Above-Mentioned Synthetic Method:

Prepared from benzoyl-protected Dasatinib (Compound 19, Pg is benzoyl) Dasatinib was yielded: Compound 1 (yield: 82.5%, purity: 99.55%).

Example 17

Synthesis of Dasatinib (Compound 1)

Under nitrogen atmosphere, methyl 2-(6-(4-(2-hydroxyethyl)piperazin-1-yl)-2-methylpyrimidin-4-ylamino)thiazole-5-formate (Compound 6) (0.5 g, 1.3 mmol), PDCP (0.2 mL, 1.5 mmol) and 2-chloro-6-methylaniline (Compound 8) (0.18 mL, 1.5 mmol) were into methylene dichloride (10 mL) by stirring and then triethylamine (0.55 mL, 4 mmol) was added by droplets when cooling to 0° C. When finish adding it reacted by stirring at room temperature overnight. Saturated sodium bicarbonate aqueous solution was added and stirred for 10 mins and then filtrated. The cake was dried to constant weight by blast at 60° C. to give Dasatinib (Compound 1) (0.2 g, yield: 32.0%)

$^1$H-NMR (300 MHz, DMSO-d$_6$): δ (ppm) 2.238 (s, 3H), 2.406-2.431 (d, 5H), 2.497-2.502 (d, 4H), 3.398-3.524 (q, 6H), 4.335-4.457 (q, 1H), 6.049 (s, 1H), 7.254-7.305 (t, 2H), 7.386-7.410 (d, 1H), 8.218 (s, 1H), 9.876 (s, 1H), 11.469 (s, 1H).

ESI (M+1): 490.33.

INDUSTRIAL APPLICATION

The synthetic routes and method of Dasatinib provided in the present invention are simple and with high yields, more suitable for industrial production.

The invention claimed is:

1. A method for synthesizing Dasatinib, comprising the following steps: the compound of Formula I:

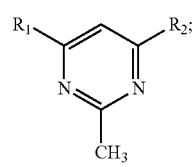

reacts with the compound of Formula II:

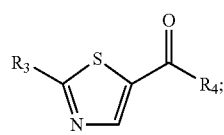

to yield the compound of Formula III:

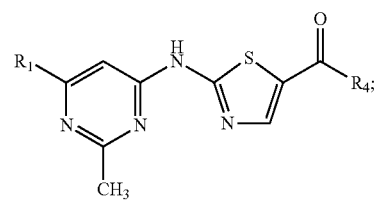

wherein, $R_1$ and $R_2$ are each independently selected from halogen, 4-(2-hydroxyethyl)piperazine-1-yl and amino; with the proviso that $R_1$ and $R_2$ are not both 4-(2-hydroxyethyl)piperazine-1-yl;

$R_3$ is selected from halo and amino, with the proviso that when either of $R_1$ and $R_2$ is amino, $R_3$ is not amino;

$R_4$ is C1-C6 alkoxy or substituted C1-C6 alkoxy, and $R_1$ in Formula I and III is halogen, the compound of Formula III reacts with 1-(2-hydroxyethyl)piperazine:

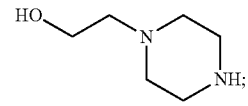

to yield the compound of Formula VII:

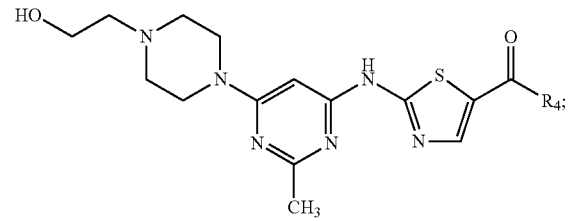

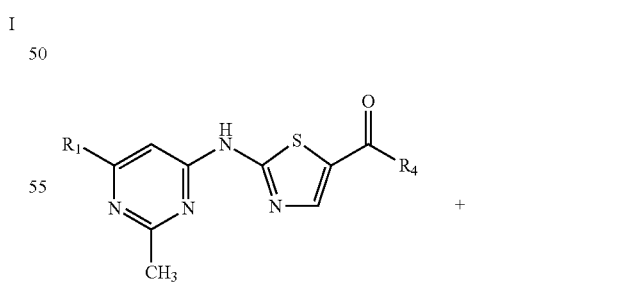

-continued

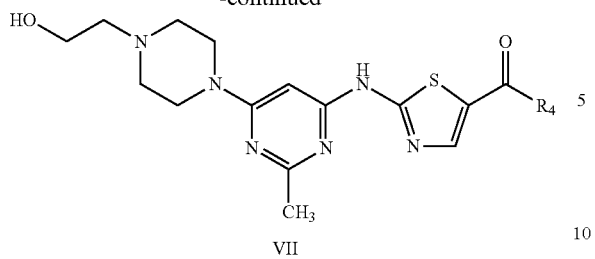
VII the compound of Formula VII is hydrolyzed to yield the compound of Formula VIII:

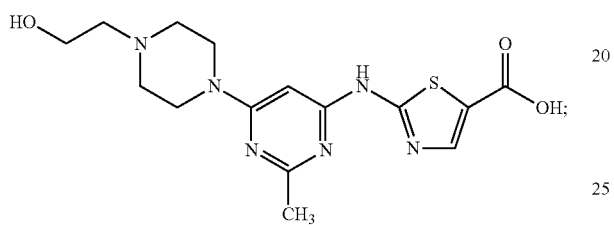
VIII the compound of Formula VIII is converted by the action of chlorination agents to be the compound of Formula IX:

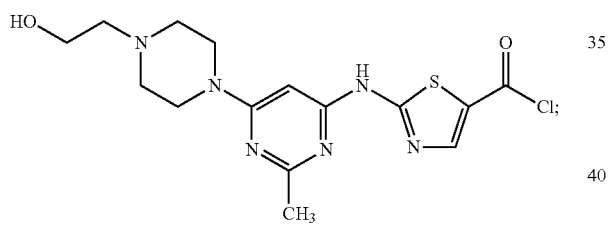
IX the compound of Formula IX reacts with 2-chloro-6-methylaniline to yield Dasatinib;

alternatively, the compound of Formula VIII reacts with 2-chloro-6-methylaniline in the presence of an amidation condensing agent to yield Dasatinib;

wherein, R4 in Formula VII is defined as the one in Formula III.

2. A method for synthesizing Dasatinib, comprising the following steps: the compound of Formula 1:

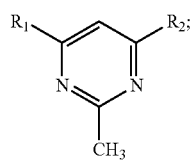
I reacts with the compound of Formula II:

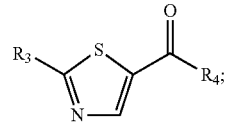
II to yield the compound of Formula III:

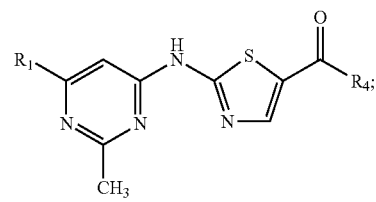
III wherein,
R$_1$ and R$_2$ are each independently selected from halogen, 4-(2-hydroxyethyl)piperazine-1-yl and amino; with the proviso that R$_1$ and R$_2$ are not both 4-(2-hydroxyethyl)piperazine-1-yl;
R$_3$ is selected from halo and amino, with the proviso that when either of R$_1$ and R$_2$ is amino, R$_3$ is not amino;
R$_4$ is C1-C6 alkoxy or substituted C1-C6 alkoxy, and
R$_1$ in Formula I and Formula III is 4-(2-hydroxyethyl)piperazine-1-yl,
the compound of Formula III is hydrolyzed to yield the compound of Formula VIII:

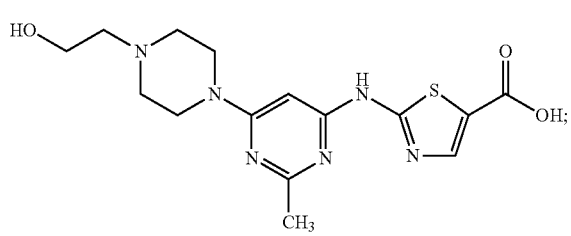
VIII the compound of Formula VIII is converted by the action of chlorination agents to be the compound of Formula IX:

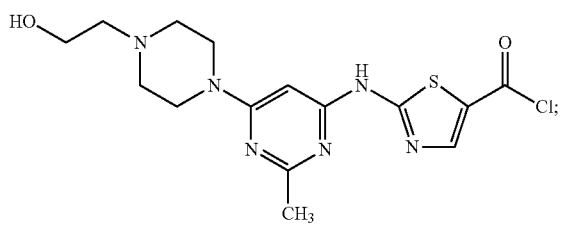
IX the compound of Formula IX reacts with 2-chloro-6-methylaniline to yield Dasatinib;

alternatively, the compound of Formula VIII reacts with 2-chloro-6-methylaniline in the presence of amidation condensing agent to yield Dasatinib.

3. The method according to claim 1, wherein, the amidation condensing agent are selected from phosphorodichloridic acid phenyl ester (PDCP), dicyclohexylcarbodiimide (DCC), diisopropylcarbodiimide (DIC), 2-(7-Aza-1H-benzotriazole-1-yl)-N,N,N',N'-tetramethyluronium hexafluorophosphate (HATU) and 1-(3-di methylaminopropyl)-3-ethylcarbodiimide (EDCI).

4. A compound of Formula III,

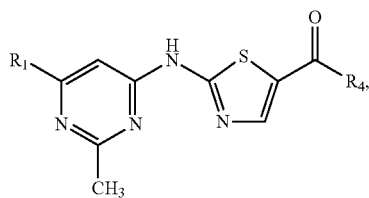

in which, $R_1$ is 4-(2-hydroxyethyl)-piperazin-1-yl;

$R_4$ is hydroxyl, methoxy, ethoxyl, propoxy, isopropoxy, butoxy, t-butoxy, sec-butoxy, isobutoxy, pentyloxy, hexyloxy chlorine or bromine.

5. The compound according to claim 4, selected from anyone of the following compounds:
methyl 2-(6-bromo-2-methylpyrimidin-4-ylamino)thiazole-5-formate;
ethyl 2-(6-bromo-2-methylpyrimidin-4-ylamino)thiazole-5-formate;
isopropyl 2-(6-bromo-2-methylpyrimidin-4-ylamino)thiazole-5-formate;
methyl 2-(6-iodo-2-methylpyrimidin-4-ylamino)thiazole-5-formate;
ethyl 2-(6-iodo-2-methylpyrimidin-4-ylamino)thiazole-5-formate;
isopropyl 2-(6-iodo-2-methylpyrimidin-4-ylamino)thiazole-5-formate;
2-(6-bromo-2-methylpyrimidin-4-ylamino)thiazole-5-formic acid;
2-(6-iodo-2-methylpyrimidin-4-ylamino)thiazole-5-formic acid;
2-(6-bromo-2-methylpyrimidin-4-ylamino)thiazole-5-formyl chloride;
2-(6-iodo-2-methylpyrimidin-4-ylamino)thiazole-5-formyl chloride;
methyl 2-(6-(4-(2-hydroxyethyl)piperazin-1-yl)-2-methylpyrimidin-4-ylamino)thiazole-5-formate;
methyl 2-(6-(4-(2-acetoxyethyl)piperazin-1-yl)-2-methylpyrimidin-4-ylamino)thiazole-5-formate;
methyl 2-(6-(4-(2-bezoyloxyethyl)piperazin-1-yl)-2-methylpyrimidin-4-ylamino)thiazole-5-formate;
methyl 2-(6-(4-(2-benzoxyethyl)piperazin-1-yl)-2-methylpyrimidin-4-ylamino)thiazole-5-formate;
methyl 2-(6-(4-(2-para-methoxybenzoxyethyl)piperazin-1-yl)-2-methylpyrimidin-4-ylamino)thiazole-5-formate;
methyl 2-(6-(4-(2-(methoxymethoxy)ethyl)piperazin-1-yl)-2-methylpyrimidin-4-ylamino) thiazole-5-formate;
methyl 2-(6-(4-(2-(methylthiomethoxy)ethyl)piperazin-1-yl)-2-methylpyrimidin-4-ylamino)thiazole-5-formate;
methyl 2-(6-(4-(2-(ethoxyethoxy)ethyl)piperazin-1-yl)-2-methylpyrimidin-4-ylamino) thiazole-5-formate;
ethyl 2-(6-(4-(2-hydroxyethyl)piperazin-1-yl)-2-methylpyrimidin-4-ylamino)thiazole-5-formate;
ethyl 2-(6-(4-(2-acetoxyethyl)piperazin-1-yl)-2-methylpyrimidin-4-ylamino)thiazole-5-formate;
ethyl 2-(6-(4-(2-bezoyloxyethyl)piperazin-1-yl)-2-methylpyrimidin-4-ylamino)thiazole-5-formate;
ethyl 2-(6-(4-(2-benzoxyethyl)piperazin-1-yl)-2-methylpyrimidin-4-ylamino)thiazole-5-formate;
ethyl 2-(6-(4-(2-para-methoxybenzoxyethyl)piperazin-1-yl)-2-methylpyrimidin-4-ylamino)thiazole-5-formate;
ethyl 2-(6-(4-(2-(methoxymethoxy)ethyl)piperazin-1-yl)-2-methylpyrimidin-4-ylamino) thiazole-5-formate;
ethyl 2-(6-(4-(2-(methylthiomethoxy)ethyl)piperazin-1-yl)-2-methylpyrimidin-4-ylamino) thiazole-5-formate;
ethyl 2-(6-(4-(2-(ethoxyethoxy)ethyl)piperazin-1-yl)-2-methylpyrimidin-4-ylamino) thiazole-5-formate;
isopropyl 2-(6-(4-(2-hydroxyethyl)piperazin-1-yl)-2-methylpyrimidin-4-ylamino)thiazole-5-formate;
isopropyl 2-(6-(4-(2-acetoxyethyl)piperazin-1-yl)-2-methylpyrimidin-4-ylamino)thiazole-5-formate;
2-(6-(4-(2-bezoyloxyethyl)piperazin-1-yl)-2-methylpyrimidin-4-ylamino)thiazole-5-isopropylformate;
isopropyl 2-(6-(4-(2-benzoxyethyl)piperazin-1-yl)-2-methylpyrimidin-4-ylamino)thiazole-5-formate;
isopropyl 2-(6-(4-(2-para-methoxybenzoxyethyl)piperazin-1-yl)-2-methylpyrimidin-4-ylamino)thiazole-5-formate;
isopropyl 2-(6-(4-(2-(methoxymethoxy)ethyl)piperazin-1-yl)-2-methylpyrimidin-4-ylamino)thiazole-5-formate;
isopropyl 2-(6-(4-(2-(methylthiomethoxy)ethyl)piperazin-1-yl)-2-methylpyrimidin-4-ylamino)thiazole-5-formate;
isopropyl 2-(6-(4-(2-(ethoxyethoxy)ethyl)piperazin-1-yl)-2-methylpyrimidin-4-ylamino) thiazole-5-formate;
2-(6-(4-(2-hydroxyethyl)piperazin-1-yl)-2-methylpyrimidin-4-ylamino)thiazole-5-formic acid;
2-(6-(4-(2-acetoxyethyl)piperazin-1-yl)-2-methylpyrimidin-4-ylamino)thiazole-5-formic acid;
2-(6-(4-(2-bezoyloxyethyl)piperazin-1-yl)-2-methylpyrimidin-4-ylamino)thiazole-5-formic acid;
2-(6-(4-(2-benzoxyethyl)piperazin-1-yl)-2-methylpyrimidin-4-ylamino)thiazole-5-formic acid;
2-(6-(4-(2-para-methoxybenzoxyethyl)piperazin-1-yl)-2-methylpyrimidin-4-ylamino) thiazole-5-formic acid;
2-(6-(4-(2-(methoxymethoxy)ethyl)piperazin-1-yl)-2-methylpyrimidin-4-ylamino)thiazole-5-formic acid;
2-(6-(4-(2-(methylthiomethoxy)ethyl)piperazin-1-yl)-2-methylpyrimidin-4-ylamino) thiazole-5-formic acid;
2-(6-(4-(2-(ethoxyethoxy)ethyl)piperazin-1-yl)-2-methylpyrimidin-4-ylamino)thiazole-5-formic acid;
2-(6-(4-(2-hydroxyethyl)piperazin-1-yl)-2-methylpyrimidin-4-ylamino)thiazole-5-formyl chloride;
2-(6-(4-(2-acetoxyethyl)piperazin-1-yl)-2-methylpyrimidin-4-ylamino)thiazole-5-formyl chloride;
2-(6-(4-(2-bezoyloxyethyl)piperazin-1-yl)-2-methylpyrimidin-4-ylamino)thiazole-5-formyl chloride;
2-(6-(4-(2-benzoxyethyl)piperazin-1-yl)-2-methylpyrimidin-4-ylamino)thiazole-5-formyl chloride;
2-(6-(4-(2-para-methoxybenzoxyethyl)piperazin-1-yl)-2-methylpyrimidin-4-ylamino) thiazole-5-formyl chloride;
2-(6-(4-(2-(methoxymethoxy)ethyl)piperazin-1-yl)-2-methylpyrimidin-4-ylamino) thiazole-5-formyl chloride;
2-(6-(4-(2-(methylthiomethoxy)ethyl)piperazin-1-yl)-2-methylpyrimidin-4-ylamino) thiazole-5-formyl chloride;
and 2-(6-(4-(2-(ethoxyethoxy)ethyl)piperazin-1-yl)-2-methylpyrimidin-4-ylamino) thiazole-5-formyl chloride.

6. The method according to claim 1, wherein, the chlorination agents are selected from phosphorus trichloride, phosphorus pentachloride, thionyl chloride and oxalyl chloride.

7. The method according to claim 2, wherein, the chlorination agents are selected from phosphorus trichloride, phosphorus pentachloride, thionyl chloride and oxalyl chloride.

8. The method according to claim 2, wherein, the amidation condensing agent are selected from phosphorodichloridic acid phenyl ester (PDCP), dicyclohexylcarbodiimide (DCC), diisopropylcarbodiimide (DIC), 2-(7-Aza-1H-benzotriazole-1-yl)-N,N,N',N'-tetramethyluronium hexafluorophosphate (HATU) and 1-(3-di methylaminopropyl)-3-ethylcarbodiimide (EDCI).

* * * * *